US008426394B2

(12) United States Patent
Podolski

(10) Patent No.: US 8,426,394 B2
(45) Date of Patent: *Apr. 23, 2013

(54) PROGESTERONE ANTAGONISTS SUCH AS CDB-4124 IN THE TREATMENT OF ENDOMETRIOSIS, UTERINE FIBROIDS, DYSMENORRHEA, BREAST CANCER, ETC

(75) Inventor: Joseph S. Podolski, The Woodlands, TX (US)

(73) Assignee: Repros Therapeutics Inc., The Woodlands, TX (US)

( * ) Notice: Subject to any disclaimer, the term of this patent is extended or adjusted under 35 U.S.C. 154(b) by 54 days.

This patent is subject to a terminal disclaimer.

(21) Appl. No.: 12/990,203

(22) PCT Filed: Apr. 27, 2009

(86) PCT No.: PCT/US2009/041826
§ 371 (c)(1),
(2), (4) Date: Oct. 28, 2010

(87) PCT Pub. No.: WO2009/134718
PCT Pub. Date: Nov. 5, 2009

(65) Prior Publication Data
US 2011/0046098 A1 Feb. 24, 2011

Related U.S. Application Data

(60) Provisional application No. 61/048,472, filed on Apr. 28, 2008.

(51) Int. Cl.
*A61K 31/573* (2006.01)
*C07J 5/00* (2006.01)
*C07J 7/00* (2006.01)

(52) U.S. Cl.
USPC .......................... 514/179; 552/595; 552/650

(58) Field of Classification Search .................. None
See application file for complete search history.

(56) References Cited

U.S. PATENT DOCUMENTS

| 4,233,296 | A | 11/1980 | Teutsch et al. |
| 6,451,780 | B1* | 9/2002 | Chwalsz et al. ............. 514/179 |
| 6,455,077 | B2 | 9/2002 | Katiyar et al. |
| 6,900,193 | B1 | 5/2005 | Kim et al. |
| 2002/0025951 | A1 | 2/2002 | Kim et al. |
| 2004/0048841 | A1 | 3/2004 | Hoffmann et al. |
| 2005/0143365 | A1 | 6/2005 | Kim et al. |
| 2007/0213306 | A1 | 9/2007 | Hausknecht |

FOREIGN PATENT DOCUMENTS

| EP | 0245170 | A1 | 11/1987 |
| WO | 83-03099 | A1 | 9/1983 |
| WO | 97-41145 | A1 | 11/1997 |
| WO | WO 97/41145 | * | 11/1997 |
| WO | 98-08471 | A1 | 3/1998 |
| WO | 00-34306 | A1 | 6/2000 |
| WO | 01-18025 | A2 | 3/2001 |
| WO | 01-74840 | A2 | 10/2001 |
| WO | 03-005954 | A2 | 1/2003 |
| WO | 2004-096151 | A2 | 11/2004 |
| WO | 2006-136462 | A2 | 12/2006 |
| WO | 2007-103510 | A2 | 9/2007 |
| WO | 2008-067086 | A2 | 6/2008 |
| WO | 2008-129396 | A2 | 10/2008 |

OTHER PUBLICATIONS

Kawaguchi, K., Fujii, S., Konishi, I., Nandu, Y., Nonogaki, H., Mori, T. American Journal of Obstretics and Gynecology 1989, 160 (3), 637-641.*
Passaro, M. D., Piquion, J., Mullen, N., Sutherland, D., Zhai, S., Figg, W. D., Blye, R., Nieman, L. K. Human Reproduction 2003, 18 (9), 1820-1827.*
Attardi, B., et al., "CDB-4124 and Its Putative Monodemthylated Metabolite, CDB-4453, are Potent Antiprogestins with Reduced Antiglucocorticoid Activity: In Vitro Comparison to Mifepristone and CDB-2914", Molecular and Cellular Endocrinology, vol. 188, No. 1-2, pp. 111-123 (2002) XP002496575 (Abstract).
Bauerfeind, I., et al., "Endocrine Agents in the Treatment of Advanced Breast Cancer," Gynakologe 199908 DE, vol. 32, No. 8, pp. 605-613 (1999).
Brueggemeier, Robert W., et al., Aromatase Inhibitors in the Treatment o Breast Cancer, Endocrine Reviews, vol. 26, No. 3, pp. 331-345 (2005).
Francis, Z., et al., "Contraception of the Future," Reproduction Humaine et Hormones 200803 FR., vol. 21, No. 1 pp. 102-116 (Mar. 2008).
International Search Report of PCT/US2010/62068 dated Aug. 17, 2011.
International Search Report of PCT/US09/041795 dated Jul. 2, 2009.
International Search Report of PCT/US09/041826 dated Jul. 3, 2009.
International Search Report of PCT/US2008/078684 dated Dec. 22, 2008.
International Search Report of PCT/US2009/041836 dated Jul. 3, 2009.
International Search Report of PCT/US2009/041841 dated Oct. 27, 2009.
International Search Report of PCT/US2010/062068 dated Aug. 17, 2011.
International Search Report of PCT/US2011/050859 dated Feb. 27, 2012.
International Preliminary Report on Patentability of PCT/US2008/078684 dated May 11, 2010.

(Continued)

*Primary Examiner* — Sreeni Padmanabhan
*Assistant Examiner* — Irina Neagu
(74) *Attorney, Agent, or Firm* — Morgan, Lewis & Bockius

(57) ABSTRACT

The present invention relates to methods of administering compositions comprising a progesterone receptor antagonist for use in treating estrogen-dependent conditions. The invention is also directed to methods for treating pain associated with endometriosis. The compositions may be administered to females with endometriosis as well as to females undergoing estrogen and/or selective estrogen receptor modulator (SERM) therapy. In certain embodiments, the invention provides a method for suppressing endometrial proliferation.

12 Claims, 3 Drawing Sheets

OTHER PUBLICATIONS

International Preliminary Report on Patentability of PCT/US2009/041836 dated Feb. 11, 2010.

International Preliminary Report on Patentability of PCT/US2010/62068 dated Sep. 25, 2012.

Kawaguchi, K., et al., "Mitotic Activity in Uterine Leiomyomas During the Menstrual Cycle," America Journal Obstet. Gynecol., vol. 160, No. 3, p. 637-641 (1989).

Leo, Joyce, C., et al., "The Activities of Progesterone Receptor Isoform A and B are Differentially Modulated by Their Ligands in a Gene-Selective Manner,", International Journal of Cancer, vol. 122, No. 1, pp. 230-243 (Jan. 2008).

Makhsida, N., et al., "Hypogonadism and Metabolic Syndrome: Implications for Testosterone Therapy," The Journal of Urology, vol. 174, Issue 3, pp. 827-834 (Sep. 2005).

Mealy, N., et al., "CDB-4124," Drugs of the Future 200411 ES, vol. 29, No. 11, pp. 1133 (2004) XP009118559.

Nabholtz, J. M., et al., "Anastrozole (Arimidex™) versus Tamoxifen as First-Line Therapy for Advanced Breast Cancer in Postmenopausal Women: Survival Analysis and Updated Safety Results," European Journal of Cancer, vol. 39, No. 12, pp. 1684-1689 (2003).

Passaro, M., et al., "Luteal Phase Dose-Response Relationships of the Antiprogestin CDB-2914 in Normally Cycling Women," Human Reproduction, vol. 18, No. 9, pp. 1820-1827 (2003).

Rose, C., et al., "An Open Randomised Trial of Second-Line Endocrine Therapy in Advanced Breast Cancer—Comparison of the Aromatase Inhibitors Letrozole and Anastrozole" European Journal of Cancer, vol. 39, No. 16, pp. 2318-2327 (2003).

Spitz., Irving M., "Progesterone Receptor Antagonists," Current Opinion in Investigational Drugs, vol. 7, No. 10, pp. 882-890 (2006) XP009110067.

Written Opinion of PCT/US2009/041836 dated Jul. 3, 2009.

Wiehle, Ronald, et al., "Anti-Progestins Suppress the Growth of Established Tumors Induced by 7,12-dimethylbenz(a) anthracene: comparison between RU486 and a new 21-substituted-19-norprogestin," Oncology Reports, vol. 18, No. 1, pp. 167-174 (2007).

Written Opinion of PCT/US2010/62068 dated Aug. 17, 2011.

U.S. Appl. No. 12/990,210—Restriction Requirement dated Apr. 22, 2012.

U.S. Appl. No. 12/245,089—Restriction Requirement dated Jun. 4, 2010.

U.S. Appl. No. 12/245,089—Non-Final Office Action dated Sep. 7, 2010.

"Repros Therapeutics Inc. Announces That Proellex Administered to Patients as Cyclic Therapy to Treat the Symptoms of Uterine Fibroids for Up to 30 Months Shows No Adverse Effects on the Endometrium," Drug Information Online—Drugs.com, pp. 1-2, Jul. 2008.

* cited by examiner

PROGESTERONE ANTAGONISTS SUCH AS CDB-4124 IN THE TREATMENT OF ENDOMETRIOSIS, UTERINE FIBROIDS, DYSMENORRHEA, BREAST CANCER, ETC

CROSS-REFERENCE TO RELATED APPLICATIONS

The present application is the National Stage of International Application Number PCT/US2009/041826, filed Apr. 27, 2009, and claims the benefit of U.S. Provisional Patent Application No. 61/048,472, filed Apr. 28, 2008, the contents of each of which is incorporated herein by reference in its entirety.

FIELD OF THE INVENTION

The present invention relates to compositions and methods for treating an estrogen-dependent condition. More specifically, the present invention relates to compositions comprising one or more progesterone antagonists for suppressing endometrial proliferation.

BACKGROUND OF THE INVENTION

Estrogens are a group of hormones essential for a variety of physiologic processes including the development of the uterus and breasts, the maintenance of bone density, and cardiovascular protection through its positive effect on lipid profiles. The effects of estrogen are mediated through its binding to estrogen receptors in the nucleus. According to the classic model, unoccupied estrogen receptor in the nucleus, upon binding estrogen, acquires the ability to interact with DNA sequences within the promoters of estrogen-responsive genes. The DNA-bound estrogen receptor modulates the transcription of these genes, either positively or negatively.

Estrogen is known to have a hyperproliferative effect on breast and uterine tissue. Administration of unopposed estrogen to menopausal women, for example, has been demonstrated to lead to both endometrial hyperplasia and endometrial cancer. In contrast, progesterone potently counteracts estrogen-dependent endometrial proliferation and cancer development. Therefore, to counteract the effects of unopposed estrogen, progestin is commonly prescribed as part of a hormone replacement therapy (HRT). However, a large clinical study from the Women's Health Initiative recently determined that the combination of conjugated estrogen and medroxyprogesterone acetate increased the risk of developing cardiovascular disease, stroke, pulmonary embolism and breast cancer. Additionally, experimental data in macaques made surgically menopausal has shown that a regimen of combined estrogen and progesterone led to higher levels of breast proliferation and hyperplasia then estrogen alone. Coadministration of progestin has also been associated with break-through bleeding, further limiting its suitability as an agent for countering the hyperproliferative effects of estrogen.

Many compounds are known in the art which affect estrogen-dependent activation of the estrogen receptor. Depending on a variety of factors these compounds may be entirely estrogenic, in that they mimic estrogen, entirely antiestrogenic, in that they block the effects of estrogen, or they may fall somewhere in-between. Compounds which exhibit mixed estrogenic and antiestrogenic properties are termed selective estrogen receptor modulators (SERMs). SERMs exert their estrogenic or antiestrogenic effects in a tissue-specific manner. The mechanism underlying this tissue-specificity is not clear, but may involve, inter alia, the recruitment of corepressor and coactivator proteins whose relative expression levels vary among tissue types and tissue-specific expression of estrogen receptor isoforms $\alpha$ and $\beta$. Estrogen receptor $\alpha$ is an activator whereas estrogen receptor $\beta$ can inhibit estrogen receptor $\alpha$ activity by forming a heterodimer with it.

The dual activities of SERMs provide several potential advantages to women. The estrogenic properties of SERMs may be used to treat or prevent diseases caused by estrogen deficiency such as osteoporosis, while minimizing some of the undesirable effects of estrogen. Conversely, the antiestrogenic properties of SERMs may be used to prevent or treat diseases such as breast cancer, in which estrogenic activity is undesirable. Nonetheless, endometrial hyperplasia has been associated with SERM therapy, thus limiting its usefulness.

The SERM tamoxifen, for example, has been shown to be antiestrogenic in the breast where it blocks the proliferative effects of estrogen and has consequently found favor as a treatment for certain types of breast cancer. On the other hand, tamoxifen displays estrogenic effects on bone and the uterus and has been associated with an increased incidence of endometrial hyperplasia and endometrial cancer, limiting it's usefulness as an antiestrogen.

A preliminary study in primates appeared to indicate that antiprogestins possess antiproliferative effects on the endometrium. However, there is concern that long-term treatment with antiprogestins could result in endometrial hyperplasia due to the action of unopposed estrogen. Several studies have demonstrated increased endometrial growth in females undergoing long-term administration of an antiprogestin which worsens with time. Moreover, several recent investigations in adult women have revealed tissue abnormalities in the endometrium of women treated with antiprogestins which appears to increase the risk of, inter alia, break through bleeding. These observations have discouraged the chronic use of antiprogestins.

There remains a need for a treatment regimen suitable for long-term administration of antiprogestins which opposes the proliferative effects of estrogen while maintaining the beneficial effects of estrogen on the body and which reduces or eliminates side-effects of chronic administration.

SUMMARY OF THE INVENTION

The instant invention relates to methods of administering compositions comprising a progesterone receptor antagonist. The progesterone antagonist may be a pure antiprogestin or a selective progesterone receptor modulator (SPRM). In a preferred embodiment, the progesterone antagonist has low affinity for glucocorticoid receptor. In another preferred embodiment, administration of the progesterone antagonist to a female does not substantially lower estrogen levels of the female. Most preferably, the progesterone antagonist is CDB-4124.

According to the invention, the compositions are administered to a female beginning at a point in the female's menstrual cycle which allows the female to undergo menstruation at the end of that cycle. Accordingly, it is preferred that the compositions be administered to a female beginning at day 14 of the menstrual cycle or thereafter. For example, the compositions may be administered beginning at day 14, 15, 16, 17, 18, 19, 20, 21, 22, 23, 24, or 25 of the female's menstrual cycle or thereafter.

In one embodiment, administration of the compositions is such that the female undergoes no further menstruations during the course of treatment. Thus, according to this embodiment, administration of the compositions begins at a point in the female's menstrual cycle that allows the female to undergo menstruation at the end of that cycle; however, the female undergoes no further menstruation during the course of the treatment.

In another embodiment, administration of the compositions allows for periodic menstruation during the course of the treatment. For example, the compositions may be administered intermittently such that the subject undergoes menses periodically during the course of the treatment. This approach is expected to avoid potentially adverse effects associated with a stagnant endometrium that may accompany extended treatment with progesterone antagonists.

The compositions may be administered to a female in order to prevent an estrogen-dependent condition in the female. Estrogen-dependent conditions that may be treated with the compositions include, without limitation, endometrial proliferation or endometrial hyperplasia.

The compositions may also be administered to a female for the prevention and/or amelioration of pain associated with disorders of the reproductive tract and disorders associated with reproductive hormone fluctuations. For example, the compositions may be administered to a female in order to prevent and/or ameliorate dyspareunia, dysmenorrhea, migraine headaches associated with the menstrual cycle, premenstrual syndrome or pain associated with dysfunctional uterine bleeding, fibroids and/or endometriosis. In a preferred embodiment, the compositions are administered to a female with endometriosis in order to treat the pain associated with endometriosis. In one aspect, the progesterone antagonists are chronically administered for treating pain associated with endometriosis.

The compositions may also be administered to a female undergoing estrogen and/or SERM therapy. In one aspect, the invention provides methods for preventing the development of endometrial hyperplasia and/or endometrial cancer in estrogen and SERM therapies.

DETAILED DESCRIPTION OF THE INVENTION

Figure 1:
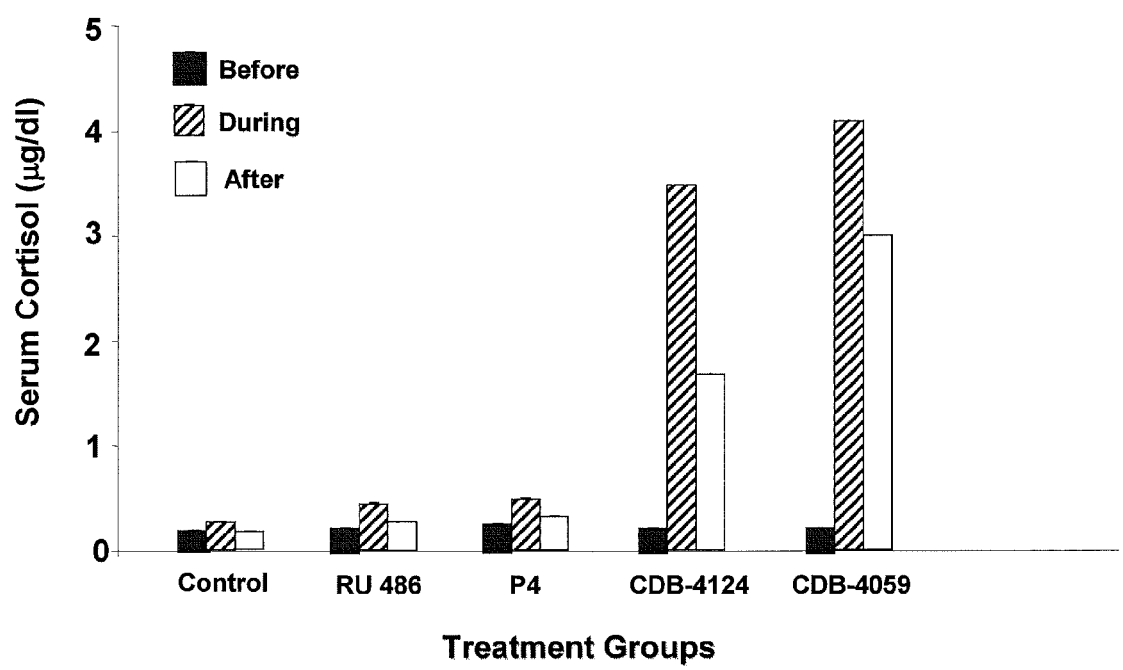
FIG. 1 is a graph depicting the effect of selective progesterone receptor modulators on serum cortisol in rats.

The term "effective dosage" means an amount of the composition's active component sufficient to achieve the desired effect which may be, e.g., suppression of endometrial proliferation or treatment of pain associated with endometriosis.

The term "estrogen-dependent condition" includes any condition associated with estrogen such as, without limitation, endometrial proliferation, breakthrough bleeding, spotting and endometrial cancer.

The term "selective progesterone receptor modulators" means compounds that affect functions of progesterone receptor in a tissue-specific manner. The compounds act as progesterone receptor antagonists in some tissues (for example, in the uterus) and as progesterone receptor agonists in other tissues.

The terms "treat" or "treatment" refer to both therapeutic treatment and prophylactic or preventative measures, wherein the object is to prevent or slow down (lessen) an undesired physiological change or disorder. For purposes of the present invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "progesterone agonist" means a compound that binds to a progesterone receptor and mimics the action of the natural hormone.

The term "progesterone antagonist" means a compound that binds to a progesterone receptor and inhibits the effect of progesterone.

The term "suppress" or "suppresses" or "suppressing" used herein in reference to proliferation of endometrial tissue means that mitotic proliferation of endometrial tissue is suppressed upon administration of a progesterone antagonist relative to untreated endometrial tissue under identical conditions and is to be distinguished from cell death via, e.g., apoptosis. The activity of a progesterone antagonist in suppressing endometrial mitotic proliferation may be tested, e.g., in a uterine cell line by, e.g., comparing the incorporation of bromodeoxyuridine (BrdU) in cells treated with a progesterone antagonist to control (untreated) cells.

The term "not substantially reduced" as used herein in reference to hormone levels in a female means that hormone levels are maintained within the normal range during administration of compositions of the invention. Thus, it is considered that some reduction in a hormone level may occur so long as the hormone level is maintained within the normal range.

The term "not substantially increased" as used herein in reference to hormone levels in a female means that hormone levels are maintained within the normal range during administration of compositions of the invention. Thus, it is considered that some elevation in a hormone level may occur so long the hormone level is maintained within the normal range.

The term "not substantially thickened" as used herein in reference to a female's endometrium means that the female's endometrium does not exceed 19 mm in thickness during the administration period, as measured by ultrasound. Thus, it is considered that some thickening may occur during the administration period so long as the female's endometrium does not exceed 19 mm in thickness. Preferably, the female's endometrium is less than 15 mm in thickness, more preferably is less than 10 mm in thickness and most preferably is less than 7 mm in thickness during the administration period. The female's endometrium may thicken by less than 100% relative to baseline measurements, more preferably thickens by less than 50% relative to baseline measurements, and most preferably thickens by less than 25% relative to baseline measurements.

The present invention relates to methods of administering compositions comprising a progesterone antagonist, preferably at doses effective to suppress endometrial proliferation. As discussed below, in the case of a six-month treatment regimen with CDB-4124, proliferation was suppressed to a greater degree when higher concentrations were administered.

It has been found that the progesterone antagonist CDB-4124, when administered for a period beginning at day 5 of a female's menstrual cycle, exhibits an inverse dose-dependency on endometrial thickness. In other words, administration of a relatively low concentration of CDB-4124 results in a substantial thickening of the endometrium during treatment. This effect is diminished when higher concentrations of CDB-4124 are administered. The methods arise from the unexpected finding that the development of cystic dilatation of the endometrial glands is the principal cause of the endometrial thickening that occurs during treatment with CDB-4124.

If treatment is begun at a time point in the female's menstrual cycle that does not allow for menstruation to occur at the end of that cycle (such as day 5 of the menstrual cycle), vascularization and glandular activity of the endometrium will occur under any residual (unblocked) progesterone causing the cystic glands to inflate and resulting in a thickening and hardening of the endometrium until CDB-4124 concentrations have built up sufficiently to block the residual progesterone. The thickened endometrium will be fragile and prone to breakdown and bleed during the course of treatment. As discussed in more detail at Example 11, relatively low concentrations of the progesterone antagonist CDB-4124, if added early in the female's menstrual cycle, result in such a thickening of the endometrium during the course of the treatment which can lead to bleeding.

According to the instant invention, administration of the progesterone antagonist begins during the luteal phase of the female's menstrual cycle allowing a menstruation to occur at the end of that cycle. Consequently, a lower concentration of progesterone antagonist may be used without the thickened endometrium that occurs when administration begins during the follicular phase. This is possible because any early-forming cystic glands are shed during menstruation at which point progesterone antagonist concentrations have accumulated to a degree sufficient to inhibit any residual progesterone. Similar advantages are expected for all antiprogestins, as morphological abnormalities have been observed for several of these compounds when administered for a period beginning during the follicular phase of the female's menstrual cycle.

Thus, in one aspect, the present invention provides a method for treating an estrogen-dependent condition comprising the administration of a composition comprising an effective amount of a progesterone antagonist to a female for a period beginning during the luteal phase of the female's menstrual cycle. The luteal phase of a female's menstrual cycle begins around day 14 of the menstrual cycle. Thus, administration of the progesterone antagonist begins at least at day 14 of the menstrual cycle. This provides the advantage of allowing the use of relatively low concentrations of progesterone antagonist without the accompanying thickening of the endometrium that occurs when the administration period begins during the follicular phase of the female's menstrual cycle.

Methods of the invention may comprise administering a composition comprising an effective amount of a progesterone antagonist for an administration period of least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more days. The composition may also be administered for an administration period of least 1, 2, 3, 4, 5, 6, 7, 8, 9, 10, 11, 12 or more months. The composition may also be administered for an administration period of at least 1, 2, 3, 4, 5, 6, 7, 8, 9, 10 or more years. During the administration period, the composition may be administered daily or periodically such as every other day, every other month, and the like. The composition may also be administered intermittently. For example, the composition may be administered for an administration period of 1, 2, 3, 4, 5 or more months, followed by a period of discontinuance, followed by an administration period of 1, 2, 3, 4, 5 or more months, and so on. In all cases, the administration period begins during the luteal phase of the female's menstrual cycle.

By "intermittent administration" it is meant a period of administration of a therapeutically effective dose of progesterone antagonist, followed by a time period of discontinuance, which is then followed by another administration period and so forth.

By "period of discontinuance" or "discontinuance period" it is meant a discontinuing of the daily, weekly, monthly or therebetween administration of progesterone antagonist. The time period of discontinuance may be longer or shorter than the administration period but is always longer than the dosing interval during the administration period. For example, where the administration period comprises daily, weekly, or monthly dosing, the discontinuance period is at least 2 days, at least 8 days or at least 32 days, respectively. Thus, the discontinuance period may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or more days.

In one embodiment, the composition is administered intermittently such that the subject undergoes menses during at least one discontinuance period. This approach is expected to avoid the adverse effects associated with a stagnant endometrium. At least one, and preferably every discontinuance period is of sufficient length for the subject to experience menstruation. More preferably, the subject experiences menstruation during every discontinuance period. In a particularly preferred embodiment, the composition is administered daily for an administration period of four months, followed by a discontinuance period during which the subject experiences menstruation, followed by another administration period of four months and so on. In all cases, the administration period begins during the luteal phase of the female's menstrual cycle.

Optionally, a gonadtropin-releasing hormone (GnRH) agonist or antagonist may administered during the discontinuance period to hasten the shedding and refreshing of the endometrium. Non-limiting examples of GnRH agonists include nafarelin, buserelin, leuprorelin, triptorelin, goserelin, [DLys$^6$]GnRH, [DAla$^6$]GnRH and the like. Non-limiting examples of GnRH antagonists include histrelin, abarelix and those found in U.S. Pat. Nos. 4,409,208, 4,547,370, 4,565,804, 4,569,927 and 4,619,914, incorporated herein in by reference in their entirety.

Optionally, a progestin may be administered during the discontinuance period in order to obtain a normal menses in the patient. Administration of a progestin preferably results in a progesterone profile that mimics the natural rise and fall of progesterone levels during menstruation. Such treatment regimens are well known in the art. Administration of a progestin during the discontinuance period may also provide opposition to the effects of estrogen in addition to that received by administration of the progesterone antagonist and therefore may help treat estrogen-dependent conditions such as thickening of the endometrium. Non-limiting examples of progestins include medrogestone, medroxyprogesterone, megestrol, norethindrone, progesterone, hydroxyprogesterone, acetoxypregnenolone, allylestrenol, cyproterone, desogestrel, dimethisterone, ethisterone, ethynodiol diacetate, gestadene, lynestrenol and the like.

In one embodiment, a female patient with endometriosis is administered a composition comprising an effective amount of a progesterone antagonist in an amount effective to suppress endometrial proliferation for a period beginning during the luteal phase of the female's menstrual cycle.

In a related embodiment, a composition comprising a progesterone antagonist is administered to a female in an amount effective to treat pain associated with a disorder of the reproductive tract and/or a disorder associated with reproductive hormone fluctuations for a period beginning during the luteal phase of the female's menstrual cycle. For example, administration of the progesterone antagonist may reduce pain associated with endometrial lesions, dysfunctional uterine bleeding, and fibroids. Pain is the most prevalent and debilitating symptom of endometriosis and is the primary indication for both medical and surgical treatment of the disease. Pain may be manifested as dysmenorrheal, pelvic pain, back pain, abdominal pain, breast pain, dyspareunia and the like. Administration of the progesterone antagonist may also reduce the size of endometrial lesions or uterine fibroids. Current regimens for the treatment of endometriosis include GnRH agonists which induce a state of pseudomenopause by inhibiting ovarian estrogen secretion and are therefore not useful for long-term administration due to loss in bone density, loss of total body calcium and other osteoporosis-like side effects. Compositions of the invention may be administered long-term with no substantial decrease in estrogen levels.

Use of the progesterone antagonists in treating pain arises in part from the unexpected finding that a preferred antiprogestin, CDB-4124, has affinity for and can inhibit the opiate µ receptor (MOP). The opiate receptors reside on the surface of nerve cells or neurons and bind endogenous opioid ligands leading to the alleviation of pain. The opiate µ receptor also appears to be involved in several aspects of female reproductive neuroendocrinology such as the control of gonadotropin release. The capacity of CDB-4124 to bind to and inhibit the opiate µ receptor is expected to extend to other antiprogestins of its class (i.e., those with the general formula below).

In another embodiment, the present invention provides methods of treating an estrogen-dependent condition associated with current hormone therapies which employ estrogenic compounds such as estrogens or SERMS by co-administering an amount of a progesterone antagonist effective to suppress endometrial proliferation, wherein the progesterone antagonist is administered for a period beginning during the luteal phase of the female's menstrual cycle. Estrogen-dependent conditions associated with current estrogen/SERM hormone therapies include, without limitation, endometrial hyperplasia and endometrial cancer. In this regard, the progesterone antagonist may be administered prior to, during, or subsequent to estrogens or SERMS as part of a combined hormone therapy regimen.

In a preferred embodiment of each method of the invention, administration of the progesterone antagonist to a female does not substantially reduce estrogen levels in the female. Thus the present invention provides an advantage over current therapies for the treatment of endometriosis which often employ gonadotropin-releasing hormone (GnRH) agonists such as Lupron® (leuprolide acetate).

In yet another preferred embodiment of each method of the invention, the progesterone antagonist exhibits reduced affinity for the glucocorticoid receptor. More preferably, the binding affinity of the progesterone antagonist for the progesterone receptor is at least 1.5 times greater than the binding affinity of the progesterone antagonist for the glucocorticoid receptor.

Any known progesterone antagonist with characteristics of the compounds described above can be used by an artisan practicing the instant invention. Particularly useful compounds include those disclosed in U.S. Pat. No. 6,900,193, hereby incorporated by reference in its entirety, as well as those disclosed in U.S. Pat. No. 6,861,415, hereby incorporated by reference in its entirety, that are 21-substituted 19-norpregnanes with a general formula:

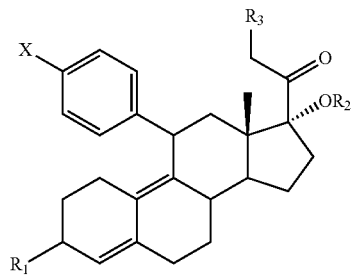

wherein:

X may be, for example alkyl, alkenyl, alkynyl, hydrogen, halogen, monoalkylamino or dialkylamino, such as N,N-dimethylamino;

$R_1$ may be, for example O, NOH or NO-methyl;

$R_2$ may be, for example hydrogen or acetyl; and $R_3$ may be, for example methyloxy, formyloxy, acetoxy, acyloxy, S-alkoxy, acetylthio, glycinate, vinyl ether, acetoxymethyl, methyl carbonate, halogens, methyl, hydroxy, and ethyloxy.

The examples of 21-substituted 19-norpregnanes include, but are not limited to, the following 24 compounds disclosed below.

1. CDB-4247 (21-propionyloxy-17α-acetoxy-11β-(4 N,N-dimethylaminophenyl)-19-norpregna-4,9-diene-3,20-dione) with the following structural formula:

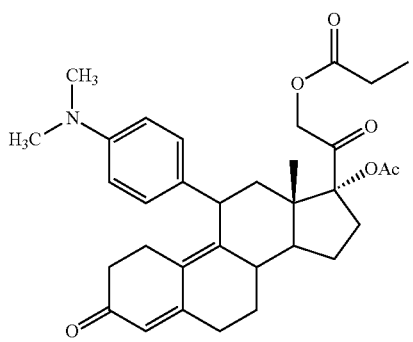 [SMILES: CCC(=O)OCC(=O)[C@@]1(OC(C)=O)CCC2C3CCC4=CC(=O)CCC4=C3C(c3ccc(N(C)C)cc3)C[C@@]21C]

2. CDB-4361 (21-vinyl ether-17α-acetoxy-11β-(4 N,N-dimethylaminophenyl)-19-norpregna-4,9-diene-3,20-dione) with the following structural formula:

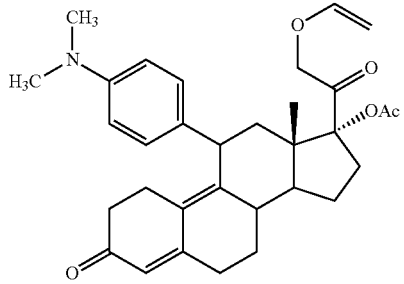 [SMILES: C=COCC(=O)[C@@]1(OC(C)=O)CCC2C3CCC4=CC(=O)CCC4=C3C(c3ccc(N(C)C)cc3)C[C@@]21C]

3. CDB-4059 (21-acetoxy-17α-acetoxy-11β-(4 N,N-dimethylaminophenyl)-19-norpregna-4,9-diene-3,20-dione) with the following structural formula:

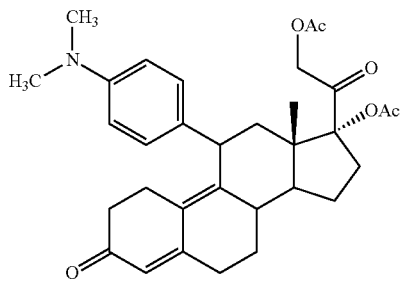 [SMILES: CC(=O)OCC(=O)[C@@]1(OC(C)=O)CCC2C3CCC4=CC(=O)CCC4=C3C(c3ccc(N(C)C)cc3)C[C@@]21C]

4. CDB-4124 (21-methoxy-17α-acetoxy-11β-(4 N,N-dimethylaminophenyl)-19-norpregna-4,9-diene-3,20-dione) with the following structural formula:

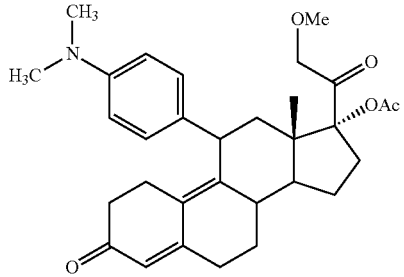

5. CDB-4031 (21-bromine-17α-acetoxy-11β-(4 N,N-dimethylaminophenyl)-19-norpregna-4,9-diene-3,20-dione) with the following structural formula:

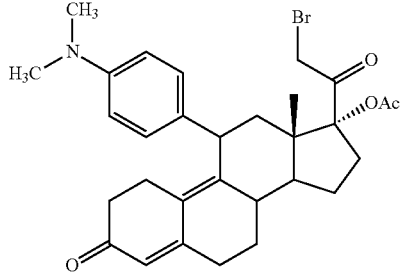 [SMILES: CC(=O)O[C@]1(C(=O)CBr)CCC2C3CCC4=CC(=O)CCC4=C3C(c3ccc(N(C)C)cc3)C[C@@]21C]

6. CDB-3876 (21-chlorine-17α-acetoxy-11β-(4 N,N-dimethylaminophenyl)-19-norpregna-4,9-diene-3,20-dione) with the following structural formula:

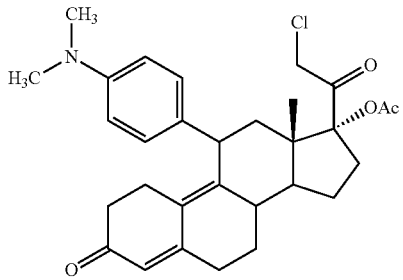

7. CDB-4058 (21-flourine-17α-acetoxy-11β-(4 N,N-dimethylaminophenyl)-19-norpregna-4,9-diene-3,20-dione) with the following structural formula:

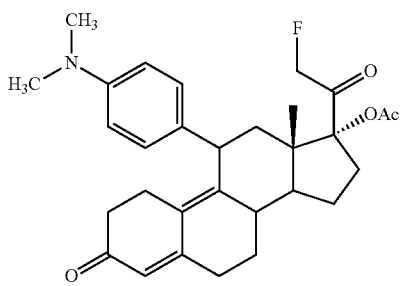

8. CDB-4030 (21-methyl-17α-acetoxy-11β-(4 N,N-dimethylaminophenyl)-19-norpregna-4,9-diene-3,20-dione) with the following structural formula:

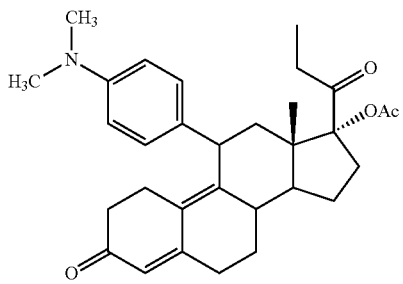

9. CDB-4152 (21-hydroxy-17α-acetoxy-11β-(4 N,N-dimethylaminophenyl)-19-norpregna-4,9-diene-3,20-dione) with the following structural formula:

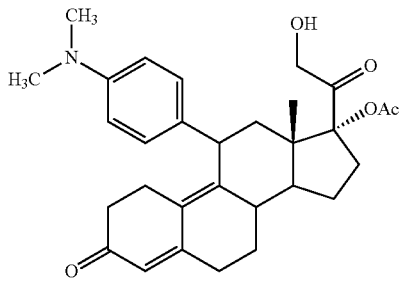

10. CDB-4167 (21-ethyloxy-17α-acetoxy-11β-(4 N,N-dimethylaminophenyl)-19-norpregna-4,9-diene-3,20-dione) with the following structural formula:

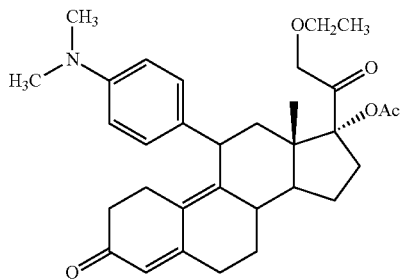 [SMILES: CCOCC(=O)[C@@]1(OC(C)=O)CCC2C3CCC4=CC(=O)CCC4=C3C(c3ccc(N(C)C)cc3)C[C@@]21C]

11. CDB-4101 (21-methoxythio-17α-acetoxy-11β-(4 N,N-dimethylaminophenyl)-19-norpregna-4,9-diene-3,20-dione) with the following structural formula:

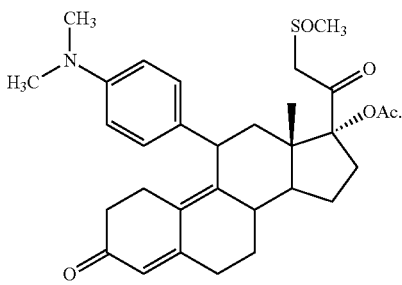

12. CDB-4110 (21-acetonide-17α-acetoxy-11β-(4 N,N-dimethylaminophenyl)-19-norpregna-4,9-diene-3,20-dione) with the following structural formula:

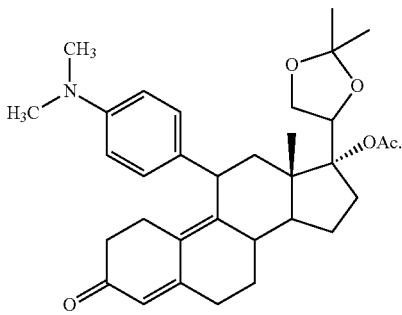 [SMILES: CC(=O)O[C@]1(C2COC(C)(C)O2)CCC2C3CCC4=CC(=O)CCC4=C3C(c3ccc(N(C)C)cc3)C[C@@]21C]

13. CDB-4111 (21-BMD-17α-acetoxy-11β-(4 N,N-dimethylaminophenyl)-19-norpregna-4,9-diene-3,20-dione) with the following structural formula:

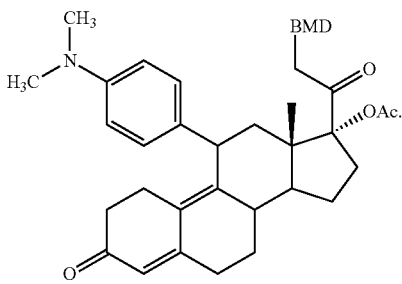

14. CDB-4125 (21-(Cyp*-hydroxy)-17α-acetoxy-11β-(4 N,N-dimethylaminophenyl)-19-norpregna-4,9-diene-3,20-dione) with the following structural formula:

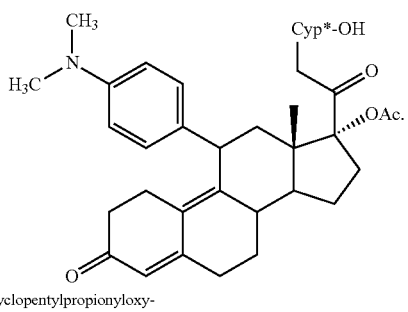

*Cyp = 3-Cyclopentylpropionyloxy-

15. CDB-4205 (3-hydroxyamino-21-methoxy-17α-acetoxy-11β-(4 N,N-dimethylaminophenyl)-19-norpregna-4,9-diene-3,20-dione) with the following structural formula:

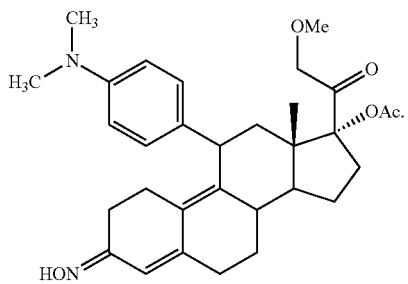

16. CDB-4206 (3-hydroxyamino-21-acetoxy-17α-acetoxy-11β-(4 N,N-dimethylaminophenyl)-19-norpregna-4,9-diene-3,20-dione) with the following structural formula:

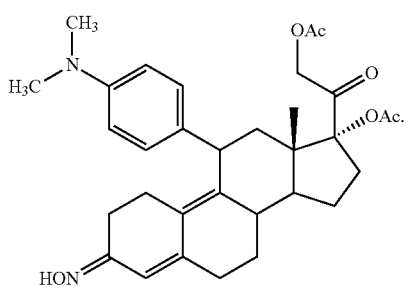

17. CDB-4226 (3-hydroxyamino-21-ethyloxy-17α-acetoxy-11β-(4 N,N-dimethylaminophenyl)-19-norpregna-4,9-diene-3,20-dione) with the following structural formula:

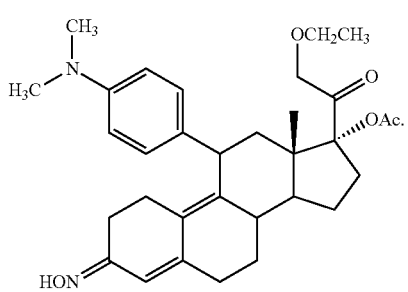

18. CDB-4262 (3-methoxyamino-21-ethyloxy-17α-acetoxy-11β-(4 N,N-dimethylaminophenyl)-19-norpregna-4,9-diene-3,20-dione) with the following structural formula:

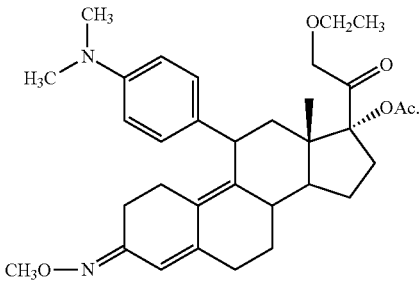

19. CDB-4223 (21-methylthio-17α-acetoxy-11β-(4 N,N-dimethylaminophenyl)-19-norpregna-4,9-diene-3,20-dione) with the following structural formula:

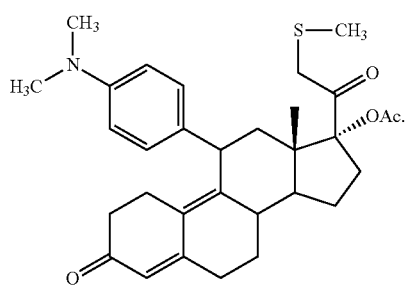 [SMILES: CSCC(=O)[C@@]1(OC(C)=O)CCC2C3CCC4=CC(=O)CCC4=C3C(c3ccc(N(C)C)cc3)C[C@@]21C]

20. CDB-4119 (4-benzoin-21-acetylthio-17α-acetoxy-11β-(4 N,N-dimethylaminophenyl)-19-norpregna-4,9-diene-3,20-dione) with the following structural formula:

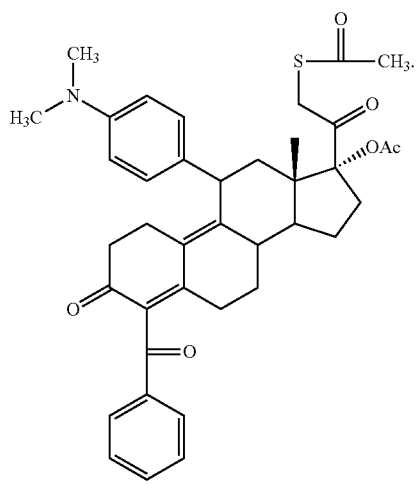 [SMILES: CC(=O)O[C@]1(C(=O)CSC(C)=O)CCC2C3CCC4=C(C(=O)c5ccccc5)C(=O)CCC4=C3C(c3ccc(N(C)C)cc3)C[C@@]21C]

21. CDB-4239 (4-benzoin-21-methoxy-17α-acetoxy-11β-(4 N,N-dimethylaminophenyl)-19-norpregna-4,9-diene-3,20-dione) with the following structural formula:

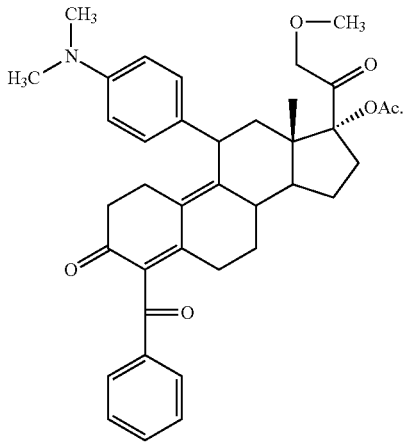 [SMILES: COCC(=O)[C@@]1(OC(C)=O)CCC2C3CCC4=C(C(=O)c5ccccc5)C(=O)CCC4=C3C(c3ccc(N(C)C)cc3)C[C@@]21C]

22. CDB-4306 (21-glycinate-17α-acetoxy-11β-(4 N,N-dimethylaminophenyl)-19-norpregna-4,9-diene-3,20-dione) with the following structural formula:

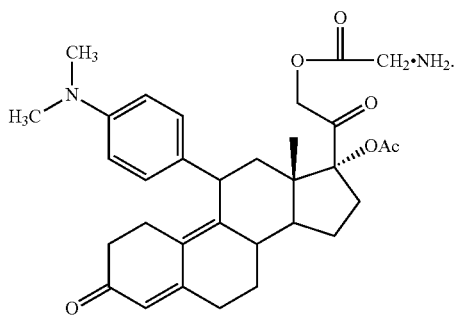

23. CDB-4352 (21-cyanothio-17α-acetoxy-11β-(4 N,N-dimethylaminophenyl)-19 norpregna-4,9-diene-3,20-dione) with the following structural formula:

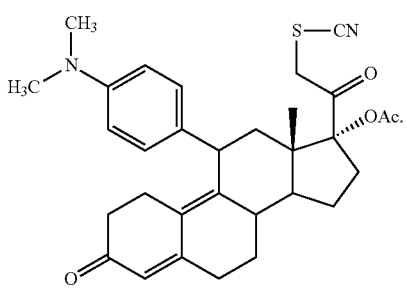 [SMILES: CC(=O)O[C@]1(C(=O)CSC#N)CCC2C3CCC4=CC(=O)CCC4=C3C(c3ccc(N(C)C)cc3)C[C@@]21C]

24. CDB-4362 (21-methoxyacetyl-17α-acetoxy-11β-(4 N,N-dimethylaminophenyl)-19-norpregna-4,9-diene-3,20-dione) with the following structural formula:

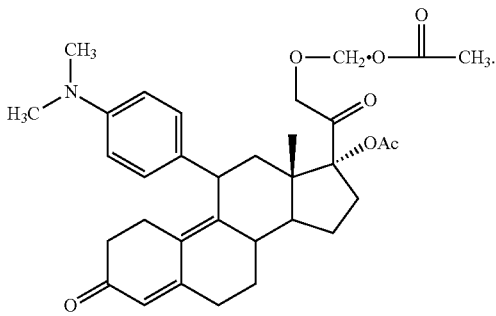

11β-monodemethylated derivatives of the 24 compounds disclosed above (i.e., those in which X is N-methylamino) are also particularly useful in practicing the instant invention. In this regard, CDB-4453 (21-methoxy-17α-acetoxy-11β-(4-N-methylaminophenyl)-19-norpregna-4,9-diene-3,20-dione), a monodemethylated derivative of CDB-4124, has been demonstrated to possess even lower anti-glucocorticoid activity than its parent. Attardi et al., 2002, Mol. Cell. Endocrin. 188:111-123, the contents of which are incorporated herein by reference.

Although compounds of the general formula above and their monodemethylated derivatives are preferred, any progesterone antagonist may be used in the practice of the present invention for its antagonist effect on the progesterone receptor. Preferably, the progesterone antagonist has one or more of the following characteristics: low antiglucocorticoid activity, minimal estrogenic and anti-estrogenic activities, and does not substantially elevate progesterone levels.

Antiprogestins which may be useful in the invention include, without limitation, asoprisnil (benzaldehyde, 4-[(11β,17β)-17-methoxy-17-(methoxymethyl)-3-oxoestra-4,9-dien-11-yl]-1-(E)-oxim; J867), its metabolite J912 (4-[17β-Hydroxy-17α-(methoxymethyl)-3-oxoestra-4,9-dien-11β-yl]benzaldehyd-(1E)-oxim), and other compounds described in DE 43 32 283 and DE 43 32 284; CDB-2914 (17α-acetoxy-11β-(4-N,N-dimethylaminophenyl)-19-nor-pregna-4,9-dien-3,20-dione) and other compounds described in Stratton et al., 2000, Hu. Reprod. 15:1092-1099; JNJ-1250132 and other compounds described in Allan et al., 2006, Steroids 71:949-954; 5-Aryl-1,2-dihydrochromeno[3,4-f] quinolines described in Zhi et al., 1998, J. Med. Chem. 41:291-302; 1,4-dihydro-benzo[d][1,3]oxazin-2-ones described in U.S. Pat. Nos. 6,509,334, 6,566,358 and 6,713,478 to Zhang et al.; 1,3-dihydro-indol-2-ones described in U.S. Pat. No. 6,391,907 to Fensome et al.; 2,3-dihydro-1H-indoles described in U.S. Pat. No. 6,417,214 to Ulrich et al.; benzimidazolones and analogues thereof described in U.S. Pat. No. 6,380,235 to Zhang et al.; 2,1-benzisothiazoline 2,2-dioxides described in U.S. Pat. No. 6,339,098 to Collins et al.; cyclocarbamates and cyclo-amides described in U.S. Pat. Nos. 6,306,851 and 6,441,019 to Santilli et al.; cyclic urea and cyclic amide derivatives described in U.S. Pat. No. 6,369,056 to Zhang et al.; and quinazolinone and benzoxazine derivatives described in U.S. Pat. No. 6,358,948 to Zhang et al.

Other antiprogestins that may be useful in the invention include, without limitation, (6α,11β,17β)-1'-(4-dimethylaminophenyl)-6-methyl-4',5'-dihydrospiro[estra-4,9-diene-17,2'(3'H)-furan]-3-one (ORG-31710) and other compounds described in U.S. Pat. No. 4,871,724; (11β,17α)-11-(4-acetylphenyl)-17,23-epoxy-19,24-dinorchola-4,9,20-trien-3-one (ORG-33628); (7β,11β,17β-11-(4-dimethylaminophenyl-7-methyl]-4',5'-dihydrospiro[estra-4,9-diene-17,2'(3'H)-furan]-3-one (ORG-31806) and other compounds described in U.S. Pat. No. 4,921,845; ZK-112993 and other compounds described in Michna et al., 1992, J. Steroid Biochem. Molec. Biol. 41:339-348; ORG-31376; ORG-33245; ORG-31167; ORG-31343; RU-2992; RU-1479; RU-25056; RU-49295; RU-46556; RU-26819; LG1127; LG120753; LG120830; LG1447; LG121046; CGP-19984A; RTI-3021-012; RTI-3021-022; RTI-3021-020; RWJ-25333; ZK-136796; ZK-114043; ZK-230211; ZK-136798; ZK-98229; ZK-98734; and ZK-137316.

Still other antiprogestins that may be useful in the invention include, without limitation, mifepristone (11β-[p-(Dimethylamino)phenyl]-17β-hydroxy-17-(1-propynyl)estra-4,9-dien-3-one; RU 486) and other described in U.S. Pat. Nos. 4,386,085, 4,447,424, 4,519,946 and 4,634,695; the phosphorus-containing 17β-side chain mifepristone analogues described in Jiang et al., 2006, Steroids 71:949-954; onapristone (11β-[p-(dimethylamino)phenyl]-17α-hydroxy-17-(3-hydroxypropyl)-13α-estra-4,9-dien-3-one) and other compounds described in U.S. Pat. No. 4,780,461; lilopristone (((Z)-11β-[(4-dimethylamino)phenyl]-17β-hydroxy-17α-(3-hydroxy-1-propenyl)estra-4,9-dien-3-one) and other compounds described in U.S. Pat. No. 4,609,651; the 11β-substituted 19-norsteroids, such as 11β-(4-Methoxyphenyl)-17β-hydroxy-17α-ethynyl-4,9-estradien-3-one described in Belagner et al., 1981, Steroids 37:361-382; the 11β-aryl-4-estrenes such as (Z)-11β-[(4-Dimethylamino)phenyl)]-17β-hydroxy-17α-(3-hydroxy-1-propenyl)estr-4-en-3-one described in U.S. Pat. No. 5,728,689; the 11β-aryl-estrene derivatives described in U.S. Pat. Nos. 5,843,933 and 5,843,931; the 11-benzaldoxime-estra-diene derivatives such as 4-[17β-Methoxy-17α-(methoxymethyl)-3-oxoestra-4,9-dien-11β-yl]benzaldehyde-1-(E)-oxime described in U.S. Pat. No. 5,693,628; the 11-benzaldoxime-17β-methoxy-17α-methoxymethyl-estradiene derivatives such as 4-[17β-Methoxy-17α-(methoxymethyl)-3-oxoestra-4,9-dien-11β-yl]benzaldehyde-1-(E)-[O-(ethylamino)carbonyl]oxime described in U.S. Pat. No. 5,576,310; the 5-substituted 11β-benzadoxime-estra-4,9-diene-carbonic acid thiolesters such as 4-[17β-Methoxy-17α-(methoxymethyl)-3-oxoestra-4,9-dien-11β-yl]benzaldehyde-1-(E)-[O-(ethylthio)carbonyl] oxime, described in WO 99/45023; the steroid esters such as (Z)-6'-(4-cyanophenyl)-9,11α-dihydro-17β-hydroxy-17α-[4-(1-oxo-3-methylbutoxy)-1-butenyl]4'H-naphtho[3',2',1'; 10,9,11]estr-4-en-3-one described in DE 19652408, DE 443-4488, DE 4216003, DE 4216004 and WO 98/24803; the fluorinated 17α-alkyl chain steroids such as 11β-(4-acetylphenyl)-17β-hydroxy-17α-(1,1,2,2,2-pentafluoroethyl)estra-4,9-dien-3-one described in WO 98/34947; the 17-spirofuran-3'-ylidene steroids such as 11 beta-(4-Acetylphenyl)-19,24-dinor-17,23-epoxy-17alpha-chola-4,9,20-trien-3-one described in U.S. Pat. No. 5,292,878; (Z)-11beta,19-[4-(3-Pyridinyl)-o-phenylene]-17beta-hydroxy-17α-[3-hydroxy-1-propenyl]-4-androsten-3-one and other compounds described in U.S. Pat. No. 5,439,913; the 13-alkyl-11-beta-phenyl gonanes such as 11beta-[4-(1-methylethenyl)phenyl]-17α-hydroxy-17beta-(3-hydroxypropyl)-13α-estra-4,9-dien-3-one described in U.S. Pat. No. 5,446,036; the 11-arylsteroids such as 4',5'-Dihydro-11beta-[4-(dimethylamino)phenyl]-6beta-methylspiro[estra-4,9-dien-17beta,2'(3'H)-furan]-3-one described in U.S. Pat. No. 4,921,845; the 11-beta-aryl-estradienes described in U.S. Pat. Nos.

4,829,060, 4,814,327 and 5,089,488; the 11-beta-aryl-4,9 gonadiens and 11-beta-aryl-13-alkyl-4,9-gonadiens described in U.S. Pat. Nos. 5,739,125, 5,407,928 and 5,273,971; the 11-beta-aryl-6-alkyl (or alkenyl or alkinyl) steroids described in EP 289073; the 10-beta,11-beta-bridged steroids described in U.S. Pat. No. 5,093,507; the 11-beta-aryl-14-beta-steroids described in U.S. Pat. No. 5,244,886; the 19,11-beta-bridged steroids described in U.S. Pat. Nos. 5,095,129, 5,446,178, 5,478,956 and 5,232,915; the 1-arylsulphonyl, arylcarbonyl and 1-arylphosphonyl-3-phenyl-1,4,5,6-tetrahydropyridazines described in U.S. Pat. No. 5,684,151; the 1-arylsulphonyl, arylcarbonyl and arylthiocarbonyl pyridazino derivatives described in U.S. Pat. No. 5,753,655; the 1,2-dihydro-[1,2-g]quinoline derivatives and 1,2-dihydro-chromeno-[3,4-f]quinoline derivatives described in U.S. Pat. Nos. 5,688,808, 5,693,646, 5,693,647, 5,696,127, 5,696,130 and 5,696,133; the oxa-steroids 6 derived from (8S,13S,14R)-7-oxa-estra-4,9-diene-3,17-dione 1 described in Kang et al., 2007, Bioorg. Med. Chem. Lett. 15:907-910; and the 7-oxa-steroids 4 described in Kang et al., 2007, Bioorg. Med. Chem. Lett. 17:2531-2534.

In the preferred embodiment, the progesterone antagonist is the antiprogestin/SPRM CDB-4124 (21-methoxy-17α-acetoxy-11β-(4 N,N-dimethylaminophenyl)-19-norpregna-4,9-diene-3,20-dione). Example 10 demonstrates that when administered to adult females for a period beginning at day 5 of the females' menstrual cycle, CDB-4124 at lower dosages (25 mg/day and 12.5 mg/day) causes a thickening of the endometrium that is not observed at high dosages (50 mg/day).

Progesterone antagonist compositions of the instant invention may be given to patients undergoing any hormone therapy associated with an increased risk or incidence of endometrial hyperplasia or endometrial cancer. These treatments may include, but are not limited to, the administration of estrogens or the administration of SERMs. Progesterone antagonist compositions of the instant invention can be also given to patients undergoing antiestrogenic treatments because the patients may benefit from antiproliferative effects that progesterone antagonist compounds exert in endometrial tissue of the uterus.

SERMs are currently administered to treat various disorders including breast cancer, osteoporosis, colon cancer, neurodegenerative diseases such as Parkinson and Alzheimer, cardiovascular disease, vaginal atrophy and obesity. However, SERM therapy is associated with endometrial hyperplasia and endometrial cancer. For example, Tamoxifen treatment of breast cancer results in about a 20% incidence of hyperplasia with atypia in women with intact uteri. Patients with endometrial specimens displaying atypia have a 25% likelihood of progressing to carcinoma. Compounds of the present invention are administered at doses sufficient to oppose the hyperplasia that accompanies treatment with SERMs. The compounds of the present invention may be administered in combination with SERMs for the treatment of any of the aforementioned disorders.

The compounds disclosed in the instant invention may act as progesterone antagonists in the uterus. The compounds of the instant invention may be suitable for the prolonged usage required in menopausal patients undergoing hormone replacement therapy, as for other indications. Where such usage is considered, the compounds preferably have only low glucocorticoid receptor binding activity and therefore, the compounds do not substantially interfere with functions of glucocorticoid receptor. Thus, the application of the compounds may have reduced side effects, such as mood swings, fatigue and weight loss, typically found when antiprogestins with a high affinity for glucocorticoid receptor are used.

In another embodiment the instant invention teaches methods that can be used for identifying compounds that possess selective progesterone receptor binding activity. These methods include receptor binding and in vivo bioassays such as anti-McGinty, anti-Clauberg, glucocorticoid, estrogenic, androgenic, anti-glucocorticoid (AG), anti-estrogen, and anti-androgen activities as well as post-coital and anti-ovulatory activities where in the leading compounds of the instant invention are used as a reference.

In another embodiment, the instant invention teaches that the potential SPRMs can be also analyzed for their effect on transcriptional activity in human cells. When SPRMs disclosed in the instant invention are used as a reference, this analysis can furnish information about (1) SPRM's interaction with receptor, (2) interaction of the activated receptor with other transcription factors, (3) activation of a transcriptional complex at a progesterone response element (PRE); and ultimately its effect on gene expression. In these experiments, plasmid expressing the hPR-B can be cotransfected with any reporter known to a person skilled in the relevant art under the PRE-dependent promoter into HeLa, HepG2 or T47D cells. The reporters may include, but are not limited to, luciferase, beta-galactosidase, green fluorescent protein, red fluorescent protein or yellow fluorescent protein. After transfection, the cells are treated with either a test compound or one of the disclosed in this application SPRMs that serves as a positive control. Following treatment, cells are assayed for reporter expression.

In another embodiment, the instant invention teaches that prospective SPRMs can be tested for their ability to oppose dexamethasone-induced cell death in human lymphocytic cell line CEM-7 and compared to effects of SPRMs disclosed in the instant specification. In these experiments, dexamethasone can be added at a concentration that results in cell death. The cells are then treated with either RU486, one of SPRMs of the instant invention or a test compound at concentrations between $10^{-6}$ and $10^{-8}$ M.

Progesterone antagonist compounds that may be used in accordance with the present invention can be synthesized using synthetic chemistry techniques known in the art such as those disclosed in U.S. Pat. No. 6,861,415. It is to be understood that certain functional groups may interfere with other reactants or reagents under the reaction conditions and therefore may need temporary protection. The use of protecting groups is described in 'Protective Groups in Organic Synthesis', $2^{nd}$ edition, T. W. Greene & P. G. M. Wutz, Wiley-Interscience (1991).

In one embodiment, compositions of the invention comprise one or more progesterone antagonists or pharmaceutically acceptable salts thereof. Depending on the process conditions the salt compound obtained may be either in neutral or salt form. Salt forms include hydrates and other solvates and also crystalline polymorphs. Both the free base and the salts of these end products may be used in accordance with the invention.

Acid addition salts may in a manner known per se be transformed into the free base using basic agents such as alkali or by ion exchange. The free base obtained may also form salts with organic or inorganic acids.

In the preparation of acid addition salts, preferably such acids are used which form suitably pharmaceutically acceptable salts. Examples of such acids are hydrochloric acid, sulfuric acid, phosphoric acid, nitric acid, aliphatic acid, alicyclic carboxylic or sulfonic acids, such as formic acid, acetic acid, propionic acid, succinic acid, glycolic acid, lactic acid, malic acid, tartaric acid, citric acid, ascorbic acid, glucuronic acid, fumaric acid, maleic acid, hydroxymaleic acid, pyruvic acid, aspartic acid, glutamic acid, p-hydroxybenzoic acid, embonic acid, ethanesulfonic acid, hydroxyethanesulfonic acid, phenylacetic acid, mandelic acid, alogenbenzenesulfonic acid, toluenesulfonic acid, galactaric acid, galacturonic acid or naphthalenesulfonic acid. All crystalline form polymorphs may be used in accordance with the invention.

Base addition salts may also be used in accordance with the invention and may be prepared by contacting the free acid form with a sufficient amount of the desired base to produce the salt in the conventional manner. The free acid form may be regenerated by contacting the salt form with an acid and isolating the free acid in the conventional manner. Pharmaceutically acceptable base addition salts are formed with metals or amines, such as alkali and alkali earth metals or organic amines. Examples of metals used as cations are sodium, potassium, calcium, magnesium and the like. Examples of suitable amines are amino acids such as lysine, choline, diethanolamine, ethylenediamine, N-methylglucamine and the like For the aforementioned purposes, the compounds of the instant invention can be administered to a patient via any conventional route where the progesterone antagonist is active. For instance, a progesterone antagonist of the instant invention can be administered orally, parenterally, sublingually, transdermally, rectally, transmucosally, topically, via inhalation, via buccal administration, or combinations thereof. Parenteral administration includes, but is not limited to, intravenous, intraarterial, intraperitoneal, subcutaneous, intramuscular, intrathecal, intraarticular, intracisternal and intraventricular. The administration form can be a tablet, capsule, pill, nasal mist, aerosol, pellet, implant (or other depot) and the like.

A therapeutically effective amount of the composition required for use in therapy may vary depending on the particular compound employed, the mode of administration, the severity of the condition being treated, the length of time that activity is desired, among other factors, and is ultimately determined by the attendant physician. In most cases, an effective dosage of a particular compound is one that is sufficient to suppress endometrial proliferation. However, in general, doses employed for human treatment typically are in the range of about 0.001 mg/kg to about 500 mg/kg per day, for example about 1 μg/kg to about 1 mg/kg per day or about 1 μg/kg to about 100 μg/kg per day. For most large mammals, the total daily dosage is from about 1 to 100 mg, preferably from about 2 to 80 mg. The dosage regimen may be adjusted to provide the optimal therapeutic response. The desired dose may be conveniently administered in a single dose, or as multiple doses administered at appropriate intervals, for example as two, three, four or more subdoses per day.

Illustratively, a composition of the invention may be administered to a subject to provide the subject with a progesterone antagonist in an amount of about 1 μg/kg to about 1 mg/kg body weight, for example about 1 μg/kg, about 25 μg/kg, about 50 μg/kg, about 75 μg/kg, about 100 μg/kg, about 125 μg/kg, about 150 μg/kg, about 175 μg/kg, about 200 μg/kg, about 225 μg/kg, about 250 μg/kg, about 275 μg/kg, about 300 μg/kg, about 325 μg/kg, about 350 μg/kg, about 375 μg/kg, about 400 μg/kg, about 425 μg/kg, about 450 μg/kg, about 475 μg/kg, about 500 μg/kg, about 525 μg/kg, about 550 μg/kg, about 575 μg/kg, about 600 μg/kg, about 625 μg/kg, about 650 μg/kg, about 675 μg/kg, about 700 μg/kg, about 725 μg/kg, about 750 μg/kg, about 775 μg/kg, about 800 μg/kg, about 825 μg/kg, about 850 μg/kg, about 875 μg/kg, about 900 μg/kg, about 925 μg/kg, about 950 μg/kg, about 975 μg/kg or about 1 mg/kg body weight.

The compositions of the instant invention may contain from about 25 to about 90% of the active ingredient in combination with the carrier, more usually between about 5% and 60% by weight.

Solid carriers may include starch, lactose, dicalcium phosphate, microcrystalline cellulose, sucrose and kaolin, while liquid carriers may include sterile water, polyethylene glycols, non-ionic surfactants and edible oils such as corn, peanut and sesame oils, as are appropriate to the nature of the active ingredient and the particular form of administration desired. Flavoring agents, coloring agents, preserving agents, and antioxidants, for example, vitamin E and ascorbic acid, may be included in preparations as well. Under ordinary conditions of storage and use, the preparations may contain a preservative to prevent the growth of microorganisms.

The compositions of the instant invention can be formulated into tablets in a tablet press by using techniques well-known to an artisan skilled in the relevant field. Optionally, the active ingredients according to the invention can also be pressed separately into two-layer tablets. According to the instant invention, tablets may include antiestrogens, estrogens or SERMs as one of the active ingredients. Compositions of the instant invention can also be formulated as an oily solution.

Patients undergoing treatments with the compositions of the instant invention should be monitored routinely for their serum estrogen and glucocorticoid levels.

The following non-limiting examples are provided to aid in understanding the teachings of the instant invention.

All patents, patent applications and publications referenced herein are hereby incorporated by reference herein to the fullest extent allowed under the law.

Example 1

Formulations of The Instant Invention Can Be Prepared As Tablets

To obtain tablets for practicing the instant invention, the following ingredients can be pressed together in a tablet press:

| | |
|---|---|
| 50.0 mg | of CDB-4124 |
| 140.5 mg | of lactose |
| 69.5 mg | of corn starch |
| 2.5 mg | of poly-N-vinylpyrrolidone |
| 2.0 mg | of aerosil |
| 0.5 mg | of magnesium stearate |

To obtain two-layer tablets for practicing the instant invention, the following ingredients can be pressed together in a tablet press:

| | |
|---|---|
| 20.0 mg | of Tamoxifen |
| 50.0 mg | of CDB-4124 |
| 105.0 mg | of lactose |
| 40.0 mg | of corn starch |
| 2.5 mg | of poly-N-vinylpyrrolidone 25 |
| 2.0 mg | of aerosil |
| 0.5 mg | of magnesium stearate |

To obtain tablets containing antiestrogens for practicing the instant invention, for example, the following ingredients can be pressed together in a tablet press:

| | |
|---|---|
| 10.0 mg | of Raloxifene |
| 50.0 mg | of CDB-4124 |
| 125.0 mg | of lactose |
| 50.0 mg | of corn starch |
| 2.5 mg | of poly-N-vinylpyrrolidone 25 |
| 2.0 mg | of aerosil |
| 0.5 mg | of magnesium stearate |

To obtain oily preparations for practicing the instant invention, for example the following ingredients can be mixed together and loaded into ampoules:

| | |
|---|---|
| 100.0 mg | of CDB-4124 |
| 343.4 mg | of castor oil |
| 608.6 mg | of benzyl benzoate |

Example 2

Compounds of the Instant Invention May Have Only Weak Antiglucocorticoid Receptor Binding Activity Certain antiprogestins were tested in receptor-binding assays for their ability to bind rabbit progesterone receptor (rbPR) and glucocorticoid receptor (rbGR). Briefly, cytosol containing PR or GR were prepared in TEGMD buffer (10 mM Tris, pH 7.2, 1.5 mM EDTA, 0.2 mM sodium molybdate, 10% glycerol, 1 mM DTT) from uterus or thymus, respectively, of estradiol-primed immature rabbits. For PR binding, the cytosol was incubated with 6 nM 1,2-[$^3$H]progesterone (50.0 Ci/mmole) and competitors were added at concentrations from 2 to 100 nM. For binding to GR, the cytosol was incubated with 6 nM 6,7-[$^3$H]-dexamethasone (40 Ci/mmol) and test compounds were added at concentrations from 20 to 100 nM. After overnight incubation at 4 C, bound and unbound [$^3$H] steroids were separated by addition of dextran-coated charcoal and centrifugation at 2100×g for 15 min at 4 C. Supernatants containing the [3H]-steroid receptor complexes were decanted into vials containing 4 ml Optifluor (Packard Instrument Co.), vortexed, equilibrated in a liquid scintillation counter for 30 minutes and then counted for 2 minutes. The $EC_{50}$ (Effective Concentration) for each standard curve and each of the compound curves was determined by entering the counting data into a four parameter sigmoidal computer program (RiaSmart® Immunoassay Data Reduction Program, Packard Instrument Co., Meriden, Conn.). Relative binding affinity (RBA) for each compound was calculated using the following equation: $EC_{50}$ of standard/$EC_{50}$ of test compound×100. The standards for the PR and GR assays were unlabeled progesterone and dexamethasone, respectively. The results of these experiments are summarized in Table 1, as a ratio of the relative binding affinities of each compound for the rbPR and rbGR receptors (rbPR/rbGR). This differential reflects the relative activity of a compound in a cell or tissue that possesses the two receptors and the requisite transcriptional cofactors.

Also given in Table 1 are the relative biological activities of the same compounds in the rabbit uterus by the anti-McGinty and anti-Clauberg assays. Compound CDB-2914 (listed at the end of the Table) was used as the control or reference compound (rabbit Biological Activity=1.00) for these experiments because results of experiments using CDB-2914 have been published before (Hild-Petito et al., 1996; Passaro et al., 1997; Reel et al., 1998; Lamer et al., 2000). For the anti-McGinty test, immature female rabbits received a subcutaneous injection of 5 µg estradiol in 10% ethanol/sesame oil daily for 6 consecutive days. On day 7, animals underwent sterile abdominal surgery to ligate a 3-4 cm segment of both uterine horns. The test compound in appropriate solvent was injected intraluminally into the ligated segment of one uterine horn and vehicle alone into the other. A stimulating dose of progesterone (267 µg/day) was administered subcutaneously to each rabbit daily for the next three days to induce endometrial proliferation. All animals were sacrificed at day 10 for removal of the uterus where a segment central to the ligatures was removed and fixed in 10% neutral buffered formalin and submitted for histological processing. Five micron sections stained with hematoxylin and cosin were evaluated microscopically for the degree of endometrial glandular proliferation. The percent inhibition of endometrial proliferation for each rabbit was calculated and the mean of the group of five animals recorded. For the Anti-Clauberg test, immature female rabbits received a subcutaneous injection of 5 µg estradiol in 10% ethanol/sesame oil daily for 6 consecutive days. On day 7, animals received progesterone by subcutaneous injection (160 µg/day) and the experimental compound in appropriate vehicle orally or subcutaneously for five consecutive days. One group of rabbits received progesterone only. Twenty-four hours after the last dose, all animals were sacrificed for removal of the uterus which was cleaned of all fat and connective tissue, weighed to the nearest 0.2 mg and placed in 10% neutral buffered formalin for subsequent histological processing. Five micron sections stained with hematoxylin and eosin were evaluated microscopically for the degree of endometrial glandular proliferation. The percent inhibition of endometrial proliferation at each dose level of the test compound was derived by comparison with progesterone-stimulated animals alone. The data presented in Table 1 (rabbit Biol. Act.) reflects the average of the results obtained for each compound by the anti-McGinty and anti-Clauberg assays relative to CDB-2914.

The tested antiprogestins were ranked on the basis of the selectivity of each compound for the rabbit PR over the rabbit GR, as listed in Table 1. The antiprogestins were also ranked on the basis of the biological activity in the rabbit uterus. Data presented in Table 1 show that the affinity of leading compounds for progesterone receptor was at least 1.5 times greater than their affinity for glucocorticoid receptor.

The results of these studies also show that the two leading compounds CDB-4124 and CDB-4059 have strong antiprogestin activity in the rabbit uterus in comparison to RU 486 and CDB-2914. Both compounds lack estrogenic, androgenic, anti-estrogenic, and anti-androgenic activities. Both compounds possess minimal anti-glucocorticoid receptor activity, a feature that distinguishes them from RU 486 and CDB-2914 which are moderately active in glucocorticoid receptor binding. In these assays, CDB-4124 performed slightly better than CDB-4059

TABLE 1

RECEPTOR BINDING AND BIOLOGICAL ACTIVITIES OF SPRMS

| SPRM | rbPR/rbGR | rabbit Biol. Act. |
|---|---|---|
| 4239 | 14.80 | 0.60 |
| 4241 | 9.10 | 0.34 |
| 4361 | 7.20 | 3.03 |
| 4306 | 5.90 | 0.95 |
| 4363 | 5.75 | 2.53 |
| 3875 | 5.11 | 1.40 |
| 4362 | 4.74 | 1.25 |

TABLE 1-continued

RECEPTOR BINDING AND BIOLOGICAL
ACTIVITIES OF SPRMS

| SPRM | rbPR/rbGR | rabbit Biol. Act. |
|---|---|---|
| 4352 | 4.21 | 0.57 |
| 4176 | 3.83 | 0.20 |
| 4243 | 2.90 | 0.00 |
| 4119 | 2.60 | 0.10 |
| 4324 | 2.16 | 1.10 |
| 4247 | 2.06 | 1.70 |
| 4205 | 1.99 | 1.00 |
| 4059 | 1.89 | 2.90 |
| 4400 | 1.76 | 2.29 |
| 3247 | 1.74 | 0.10 |
| 4167 | 1.69 | 1.50 |
| 4124 | 1.58 | 3.60 |
| 4226 | 1.51 | 0.54 |
| 4206 | 1.44 | 0.68 |
| 4416 | 1.33 | 0.77 |
| 4417 | 1.31 | 0.70 |
| 4111 | 1.30 | 0.36 |
| 4125 | 1.19 | 1.55 |
| 4223 | 1.17 | not given |
| 4398 | 1.16 | 0.99 |
| 4058 | 1.08 | 0.90 |
| 4418 | 1.03 | 0.25 |
| 4177 | 1.03 | 0.00 |
| 4030 | 0.96 | 0.30 |
| 4374 | 0.95 | 2.25 |
| 4399 | 0.93 | 0.35 |
| 4152 | 0.82 | 1.40 |
| 4110 | 0.70 | 0.10 |
| 4031 | 0.69 | 0.70 |
| 4101 | 0.61 | 0.65 |
| 4248 | 0.42 | 0.00 |
| 4227 | 0.38 | 0.00 |
| 4393 | 0.35 | 0.00 |
| 4396 | 0.18 | not given |
| 2914 | 1.07 | 1.00 |

Example 3

Measuring Cortisol

Several different experimental systems support a conclusion that RU 486 increases cortisol because RU 486 has strong anti-glucocorticoid properties in humans and primates.

However, as shown in FIG. 1, rats treated with RU 486 at 10 mg/kg showed no significant difference in the levels of cortisol. In contrast, rats treated with either CDB-4124 or CDB-4059 at the same dose levels had significantly higher levels of serum cortisol than rats from a control group.

Figure 2:
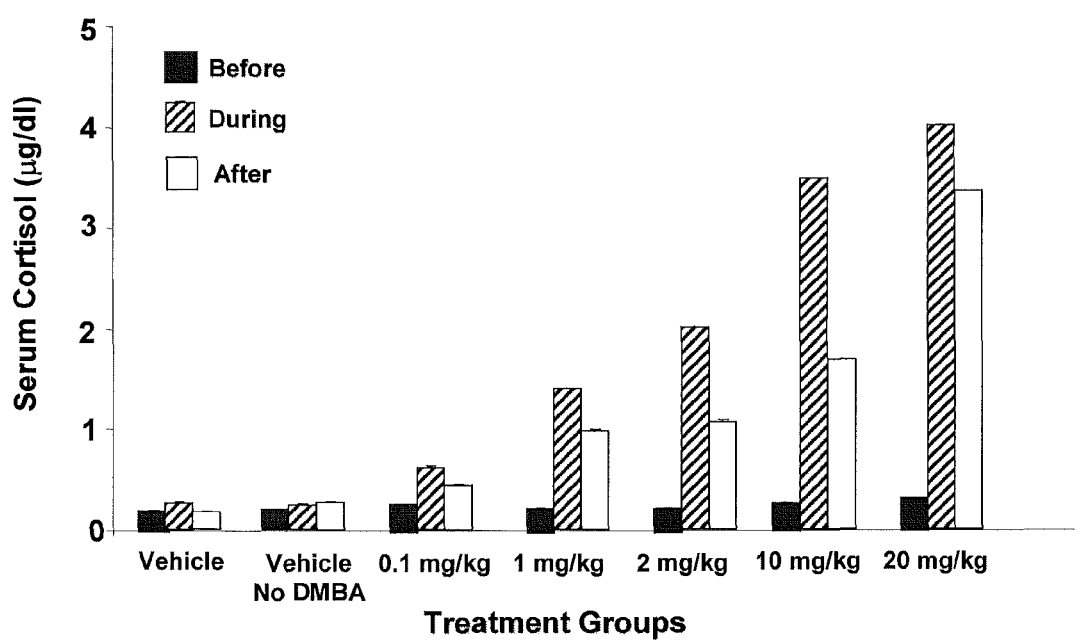
FIG. 2 is a graph depicting the dose-dependent effect of CDB-4124 on serum cortisol in rats.

These higher levels were in the range of 3-4 ug/dl (30-40 ng/ml). The effects were dose-dependent in that increasing doses of CDB-4124 led to increased cortisol (FIG. 2).

This difference in effects of RU 486 versus CDB-4124 or CDB-4059 on cortisol levels can be explained by assuming that after 21 days of chronic dosing, a rat liver was able to metabolize RU 486 better than either of the two CDB compounds.

Example 4

Measuring Corticosterone

Corticosterone is the most abundant glucocorticoid in rats. The effects of the SPRMs on cortisol shown in FIGS. 1 and 2 may be secondary to strong effects on corticosterone. To better explore this phenomenon, the levels of corticosterone were measured in groups, which showed the strongest changes in cortisol levels, such as groups treated with CDB-4124 at 20 mg/kg or 10 mg/kg. For comparison, the following groups were also assayed: a group that received 20 mg/kg CDB-4124 plus 10 mg/kg progesterone, a group that received 10 mg/kg CDB-4124 plus 10 mg/kg progesterone, a group that received 10 mg/kg RU 486, a group that received 10 mg/kg of progesterone alone, a control group. The levels of corticosterone were 10-40 times higher than the levels of cortisol. However, almost no difference between groups with respect to mean corticosterone levels was observed. There were no differences among the groups before treatment (p=0.43, Kruskal-Wallis test), after 21 days of treatment (p=0.57, Kruskal-Wallis test), or after 28 days of treatment and at sacrifice (p=0.061, Kruskal-Wallis test.

To measure effects of exogenous progesterone on serum corticosterone, the levels of corticosterone were compared in 3 paired groups that differed in whether they received exogenous progesterone (e.g., comparisons of control versus progesterone or CDB-4124 at 20 mg/kg versus CDB-4124 at 20 mg/kg plus progesterone, or CDB-4124 at 10 mg/kg versus CDB-4124 at 10 mg/kg plus progesterone). There was a statistically significant difference detected: the levels of corticosterone were lowered in animals treated with progesterone after 21 days of treatment (p=0.029, Mann-Whitney Wilcoxon test, two-tailed). This effect was not verified in sera taken at sacrifice. No differences in serum corticosterone were found between the progesterone and the CDB-4124 groups, the progesterone and the RU-486 groups, or the RU-486 group and the CDB-4124 groups.

The relationship between serum cortisol and serum corticosterone in each group was also examined. There was a strong positive linear correlation between the two for CDB-4124 at 20 mg/kg ($r^2$=0.78), for CDB-4124 at 10 mg/kg ($r^2$=0.82), and for RU 486 ($r^2$=0.85). Adding progesterone to the first two CDB-4124 groups made the relationship far less strong ($r^2$=0.34 for Group 10 and $r^2$=0.37 for Group 11, respectively). Progesterone itself showed no such positive relationship ($r^2$=−1.0). The control group demonstrated no relationship between the two glucocorticoids ($r^2$=0.064). Thus, increased levels of cortisol in groups receiving CDB-4124 are correlated to levels of corticosterone, due perhaps to conversion from corticosterone that is somehow enhanced. This is consistent with an effect of CDB-4124 seen above: an effect on metabolic enzymes responsible for levels of progesterone and cortisol.

Although no strong effect of CDB-4124 on the primary glucocorticoid of the rat was found, nevertheless, for safety reasons, patients given CDB-4124 or CDB-4059 in Phase I clinical trials should be monitored for possible anti-glucocorticoid effects including a possible increase in serum cortisol, corticosterone, or ACTH.

Example 5

Testing Anti-Proliferative Effects of SPRMs in Uterine Cells

Any uterine cell lines can be used. Proliferation is measured in 96-well microtiter plates. $5 \times 10^3$ cells are added to each well. Culture medium and drug solutions are added to wells with a Perkin Elmer Cetus PRO/PETTE. The culture medium is IMEM supplemented with 5% fetal bovine serum. Eight drug concentrations are tested, in duplicate, from 0.078 uM to 10 uM. Samples include tamoxifen alone and each of the compounds disclosed in the instant specification in combination with tamoxifen.

After a four-day incubation, the medium is replaced with fresh medium containing drug, and after a total of seven days, the cell monolayers are fixed with trichloracetic acid and stained with sulforhodamine dye. Absorbances (492 nm) of the extracted dye solutions are measured with a Titertek Multiscan plate reader. Dose response curves (percent of control absorbances vs. drug concentrations) are constructed in order to estimate $IC_{50}$ values defined as the drug concentrations (micromolar) which inhibited 50% proliferation. $IC_{50}$ values are correlative with a potency of a tested drug in inhibiting cell proliferation and therefore provide information required to identify compounds suitable for preventing hyperproliferation of the uterine cells.

Example 6

CDB-4124 Lowers Luteal Phase Progesterone in Cynomolgus Monkeys

Cynomolgus monkeys (*Macaca fascicularis*) (n=14) were treated orally for 36 weeks with CDB-4124 or RU-486 at 1.0 mg/kg/day or with placebo (control). Another group (n=14) received Lupron® IM once per month. Urinary progesterone levels were measured for each animal for one month during the middle of the study (weeks 14-17) and for the last month of the study (weeks 33-36). The results are presented below:

|  | Decrease in luteal phase progesterone | No decrease in luteal phase progesterone |
| --- | --- | --- |
| Controls | 1 | 13 |
| Lupron ® | 13 | 1 |
| RU 486 | 9 | 5 |
| CDB-4124 | 8 | 6 |

Example 7

CDB-4124 Does Not Lower Follicular Phase Estrogen in Cynomolgus Monkeys

Urinary estrogen levels were measured for each animal of Example 6 for one month during the middle of the study (weeks 14-17) and for the last month of the study (weeks 33-36). The follicular phase results are based on 35 baseline ovulating cycles. The results are presented below:

|  |  | Mean | Sd | Lower? |
| --- | --- | --- | --- | --- |
| Follicular Phase |  | 68.3 | 19.6 |  |
| Controls | Week 18 | 81.5 | 27.4 | No |
|  | Week 36 | 86.3 | 23.8 | No |
| Lupron ® | Week 18 | 49.9 | 19.3 | Yes |
|  | Week 36 | 41.7 | 13.4 | Yes |
| RU 486 | Week 18 | 67.4 | 27.1 | No |
|  | Week 36 | 64.8 | 30.0 | No |
| CDB-4124 | Week 18 | 63.8 | 24.6 | No |
|  | Week 36 | 67.3 | 22.9 | No |

Example 8

CDB-4124 and Lupron® but not RU 486 Suppress Proliferation in Cynomolgus Monkey Endometrial Epithelia At week 36, three animals from each group of Example 6 were injected within 24 hours of sacrifice with the thymidine analog bromodeoxyuridine (BrdU), a marker of proliferating cells and their progeny, to assess tissue proliferation. Full thickness uterine sections were stained and examined microscopically for evidence of proliferation in terms of the % cells positive for incorporation of BrdU:

| TXT | Uterus epithelium Brdu-% | Uterus stroma Brdu-% | Breast Brdu-% |
| --- | --- | --- | --- |
| Control | 10.0 ± 2.5 | 2.6 ± 0.6 | 2.4 ± 1.1 |
| Lupron ® | 3.1 ± 0.8 | 2.2 ± 1.0 | 0.3 ± 0.1 |
| RU 486 | 12.6 ± 1.8 | 3.1 ± 1.0 | 0.9 ± 0.3 |
| CDB-4124 | 2.1 ± 2.2 | 1.1 ± 0.25 | 1.9 ± 0.7 |

Example 9

CDB-4124 and RU 486 but not Lupron® Enhance Apoptosis in Cynomolgus Monkey Endometrial Epithelium Apoptosis was assessed in tissue from the same animals on slides by the terminal deoxynucleotidyl transferase mediated dUTP-biotin nick end labeling (TUNEL) technique. The percent apoptotic cells is presented below:

| TXT | Uterus epithelium Apo % | Uterus stroma Apo % | Breast Apo % |
| --- | --- | --- | --- |
| Control | 0.2 ± 0.1 | 0.7 ± 0.2 | 0.5 ± 0.3 |
| Lupron | 0.2 ± 0.1 | 0.2 ± 0.1 | 1.4 ± 0.7 |
| RU 486 | 0.5 ± 0.1 | 0.5 ± 0.1 | 1.2 ± 0.6 |
| CDB-4124 | 0.5 ± 0.2 | 0.5 ± 0.1 | 2.6 ± 0.9 |

Example 10

Low Concentrations of CDB-4124 Increase Endometrial Thickness During an Administration Period Beginning at Day 5 of a Female's Menstrual Cycle Thirty-nine pre-menopausal adult women diagnosed with endometriosis were the subject of a six month study of Proellex™ (CDB-4124) in the treatment of endometriosis. The study included three dose levels of CDB-4124 as well as a positive control arm. The positive control was Lucrin®, a GnRH agonist, commonly used for the treatment of endometriosis (also known as Lupron®). CDB-4124 was administered in a double blinded fashion as a daily oral capsule at dosages of 12.5 mg/day (n=2), 25 mg/day (n=3) and 50 mg/day (n=3), beginning at day 5 of the women's menstrual cycle. Another group (n=4) were injected with a slow release formulation of Lucrin® once per month as a positive control.

All doses of CDB-4124, as well as the Lucrin® dose, on average reduced distress related to pain over the course of the six month exposure to the drug, with the 50 mg CDB-4124 dose reducing both the duration and intensity of pain more effectively than the 12.5 mg or 25 mg doses and is significantly better (p=0.0012) than Lucrin® in reducing the number of days of pain over the course of the study. Pain reduction also occurred more rapidly than with the active control, Lucrin®. The response of pain to treatment in this study was analyzed in two ways. Patients in the study maintained daily pain diaries to record the severity and frequency of pain. In addition, at each office visit, patients filled out endometriosis symptom surveys that included a questionnaire that evaluated intensity of pain on a bad day on a scale of 0-10 with 10 being the greatest intensity. Daily pain diaries indicated that on average, women on Lucrin® experienced 19.4 days of pain over the first three months. Women on 50 mg of CDB-4124 exhibited less than 1 day of pain over the same period. Women on 25 mg and 12.5 mg of CDB-4124 exhibited more days of pain than that recorded by women receiving the highest dose of CDB-4124 or Lucrin®. There appeared to be a dose dependent effect on pain reduction. Over the 180 day treatment period, pain diaries indicated that women on the 50 mg CDB-4124 dose had 170 or 96% pain free days (standard deviation=8.86 days). This decrease in duration of pain was statistically better (p=0.0012) than the 117.8 (74%; standard deviation 51.4 days) pain free days achieved with Lucrin®. The 50 mg dose of CDB-4124 was also statistically superior to both the 25 mg and the 12.5 mg doses with regard to pain free days. Patients on CDB-4124 12.5 mg and 25 mg doses had 115.9 (66%; standard deviation 69.2 days) and 133.6 (75%; standard deviation 27.4 days) pain free days, respectively. These results clearly support a dose response for CDB-4124. The 25 mg and 12.5 mg doses of CDB-4124 were not statistically different from Lucrin®. At the end of the first month of therapy there was a statistically significant reduction in days of pain in the 50 mg Proellex group (p=0.031) compared with baseline, but not in the three other treatment groups. The intensity of pain was assessed by the question: "On a scale of 1-10, with 0 being no pain and 10 being extreme pain, how intense was your pain on a bad day?" The mean scores for intensity of pain at baseline were 6.3 for the CDB-4124 groups and 6.1 for the Lucrin® group. Statistically significant relief from pain was evident by the first month in the 25 mg and 50 mg Proellex groups. At month three all four active treatment groups had statistically significant reduction in pain compared with baseline, with the following scores: 3.7 (p=0.03) for 12.5 mg CDB-4124, 3.2 (p=0.03) for 25 mg CDB-4124, 1.6 (p=0.015) for 50 mg CDB-4124 and 1.5 (p=0.016) for Lucrin®. These dose related reductions continued until month six when the values for pain intensity were 2.0 (p=0.008), 2.8 (p=0.023), 0.6 (p=0.004) and 0.7 (p=0.016), respectively. Two months after stopping treatment pain returned and was of similar intensity in all four treatment groups.

Women receiving Lucrin® in the study, on average, experienced a reduction of estrogen to post-menopausal levels (<20 pg/ml) by month three and this was maintained through month six of treatment. This outcome was associated with a statistically significant increase (p=0.023) in biomarkers of bone resorption compared with the baseline values at month three, and therefore an increased risk of bone loss. At month six as well as at the one-month follow up visit, this increase in markers of bone resporption was still present in women treated with Lucrin®. All doses of CDB-4124 maintained estrogen concentrations significantly above those seen with Lucrin® and remained in the low normal range (mean>40 pg/ml). Importantly, there were no significant changes in biomarkers of bone resorption in any of the dose arms of CDB-4124 at three and six months of treatment. Women with post-menopausal levels of estrogen have been shown to be at greater risk for bone loss and other medical conditions. Lucrin®, therefore, is not indicated for treatment lasting longer than six months.

Side effects of CDB-4124 were generally mild with no individual organ system being involved systematically. Although this was a small study and no definitive conclusions can be made from the safety data, there was no single signal of safety observed.

Women in the study were closely monitored for changes in the structure of the endometrium. Data from these examinations suggest an inverse dose dependent effect of CDB-4124 on endometrial thickness, as measured by ultrasound. Comparisons were made to both baseline and visit one ultrasound measurements of endometrial thickness. The clinical data showed that progressive endometrial thickening occurs with all three doses of CDB-4124. The endometrial thickening was most prominent with the 12.5 mg dose and less so with the 25 mg and 50 mg doses. After six months of treatment, the 12.5 mg dose resulted in a statistically significant increase of 10.9 mm (p 0.016) in endometrial thickness from baseline while the 25 mg and 50 mg doses showed a statistically insignificant change of 9.8 mm and 3.9 mm respectively.

Four subjects who experienced significant bleeding in the study all had an endometrial thickness of more than 20 mm and had been on treatment for 5 months or longer. In a separate study, women with uterine fibroids were administered daily doses of 12.5 mg, 25 mg or 50 mg CDB-4124 for a three month period, beginning at day 5 of each woman's menstrual cycle. None of the subjects receiving the 12.5 mg or 25 mg doses had a significant bleeding episode and their mean endometrial thickness measurements were less than 20 mm. These data suggest that the risk of bleeding is related to both duration of therapy and increased endometrial thickness.

Example 11

Endometrial Biopsies of Women in the CDB-4124 Treatment Groups

Endometrial biopsies were taken from 27 women exposed to 12.5 mg, 25 mg or 50 mg CDB-4124 for six months and 31 women with uterine fibroids exposed to 12.5 or 25 mg CDB-4124 for three months. Specimens were evaluated in a treatment blinded fashion utilizing the WHO diagnostic schema (Silverberg et al., tumors of the uterine corpus: epithelial tumors and related lesions. Tavassoli F A, Stratton M R, reditors. WHO Classification of Tumors: Pathology and Genetics of Tumors of the Breast and Female Genital Organs. Lyon, France: IARC Press, 2003: 221-232). A consensus primary end point result was determined for each specimen by majority (two or more of three pathologists agree), or in the event of all pathologists disagreeing the "worst" diagnosis of the three was assigned. Additional findings were recorded using a structured data collection instrument. All raw data was provided to the reviewing pathologists, who undertook an independent analysis that was the basis for their conclusions.

The results demonstrated a consensus primary diagnosis in all CDB-4124 treated subjects of benign endometrium, without any hyperplasias, endometrial intraepithelial neoplasia, or carcinomas. Thus, CDB-4124 suppressed endometrial proliferation at every concentration tested. The results for the primary diagnosis were no different between the subjects with endometriosis or uterine fibroids or the subjects exposed for three or six months or among the three different doses.

Additional secondary findings within the "benign" category were noted, the most prominent being the presence of cystic dilation of glands similar to the histological pattern recently described for women treated with other progesterone receptor modulators such as asoprisnil, mifepristone and CDB-2914. The glandular epithelium within these cysts varied in appearance, but contained non-physiologic combinations of poorly developed secretory activity, dying cells (apoptotic bodies) and rare mitoses. Other cystic glands were lined by inactive epithelium. Rare glandular mitoses seen at low doses of CDB-4124 disappeared at 50 mg, suggesting an antiproliferative benefit with increasing dose. This constellation of cysts and epithelial findings are novel and fall within the spectrum of progesterone receptor modulator associated endometrial changes recently described for other compounds in this class. CDB-4124 did not induce, however, the blood vessel wall thickening and latticed capillary patterns seen with some other progesterone receptor modulators.

Importantly, across all treatment doses, a positive correlation was observed between increased endometrial thickness as measured by ultrasound and the diagnosis of cystic glands by the reviewing pathologists. However, in females receiving the lowest doses of CDB-4124, cystic glands were more prominent in number and size than in females receiving the highest dose. There was a clear trend in the 12.5 mg group for increasing thickness and more cysts between the 3 and 6 months time points. This association of endometrial thickness with histologic cysts, which becomes stronger with increasing duration of therapy, suggests that the thickening of the endometrium is due to the development of glandular dilatation. Importantly, administration of CDB-4124 to each treatment group began on day 5 of the females' menstrual cycle and consequently, no menstruation occurred in females of any of the treatment groups until the drug was removed.

Figure 3:
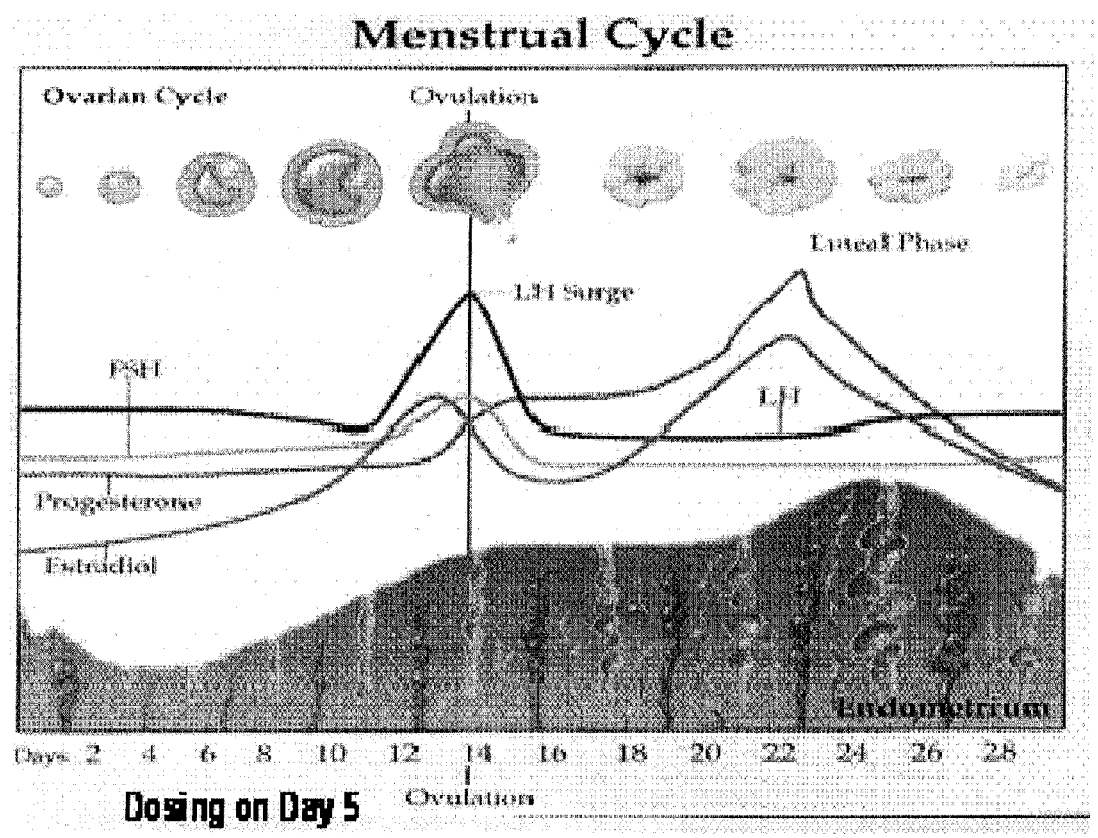
FIG. 3 is a time-line of the female menstrual cycle. Vascularization and glandularization of the endometrium is depicted as beginning at around day 5 of the menstrual cycle with a dramatic increase at day 14 and thereafter under the influence of progesterone.

It is known that extensive glandularization of the endometrial bed begins to occur soon after day 5. See FIG. 3. Vascularization and further glandular activity is hastened under the influence of progesterone starting around day 14. Without wishing to be bound by theory, it is believed that, in contrast to females in the 50 mg treatment group, CDB-4124 has not accumulated in females in the 12.5 mg and 25 mg treatment groups to a concentration sufficient to completely block progesterone during the females' first cycle, causing the cystic glands to swell in size and number under the influence of residual (unblocked) progesterone stores.

Administration of CDB-4124 beginning at a time point during the luteal phase (i.e., day 14 or thereafter) of a female's menstrual cycle will allow the female to menstruate during the initial cycle. It is expected that any early forming cystic glands will be shed during this menses, after which CDB-4124 concentrations are expected to be sufficiently high to block progesterone and thereby inhibit progesterone's vascular and glandular effects on the endometrium. Accordingly, the instant invention provides a dosing regimen for treatment of, inter alia, estrogen-dependent conditions comprising the administration of relatively low concentrations of progesterone antagonists such as CDB-4124, without unwanted thickening and increased friability of the endometrium. Thus, the presently disclosed dosing regimen provides the advantage of reducing or eliminating, for example, breakthrough bleeding that accompanies thickened, friable endometria, without the need for inducing periodic menstruations during progesterone antagonist treatment. It is expected that beneficial results will also be obtained (to a relatively lesser extent) where higher concentrations of CDB-4124 are administered for a period beginning during the luteal phase of the female's menstrual cycle. Thus, where, e.g. 50 mg of CDB-4124 are administered for a period beginning at a time point in the luteal phase of a female's menstrual cycle, further reductions in endometrial thickness are expected relative to those observed in the 50 mg treatment group of Example 10 (for whom the administration period began at day 5 of each female's menstrual cycle).

Example 12

Administration of Low Concentrations of a Progesterone Antagonist for Treating Endometriosis Females suffering from endometriosis are divided into two groups: a first group receives 12.5 mg of CDB-4124 for a six-month period beginning at day 5 of each female's menstrual cycle; a second group receives 12.5 mg of CDB-4124 for a six-month period beginning at day 15 of each female's menstrual cycle. Endometrial thickness is monitored regularly throughout the six-month period. Females in the second group exhibit a lesser degree of endometrial thickening than those in the first group and preferably an absence of endometrial thickening while benefiting from reduced endometrial-induced pain.

I claim:

1. A method for treating an estrogen dependent condition selected from the group consisting of endometriosis and uterine fibroids comprising intermittent administration of a composition comprising a selective progesterone receptor modulator (SPRM) at a dose of 12.5 mg to 25 mg to a female in need thereof, said intermittent administration comprising administering said composition daily or every other day for a period of at least 30 days beginning during the luteal phase of said female's menstrual cycle, then discontinuing said administration by means of a continual lack of treatment for a period of days sufficient to allow the female to menstruate then administering the composition daily or every other day for a period of at least 30 days, then discontinuing said administration b means of a continual lack of treatment for a period of days sufficient to allow the female to menstruate, and repeating this pattern of administration and discontinuance of administration for as long as necessary to achieve treatment of said conditions.

2. The method of claim 1, wherein the estrogen dependent condition is endometriosis.

3. The method of claim 1, wherein treatment is initiated at from day 14 to day 25 of said female's menstrual cycle.

4. The method of claim 1, wherein the SPRM is a compound of formula (I):

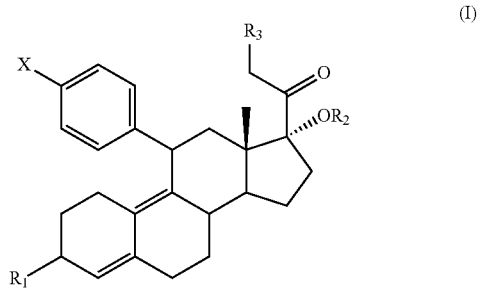

or a pharmaceutically acceptable salt, hydrate or solvate thereof, wherein:
  X represents an alkyl, alkenyl, alkynyl, hydrogen, halogen, monoalkylamino or dialkylamino;
  $R_1$ represents =O, =NOH or =NO-methyl;
  $R_2$ represents a hydrogen or acetyl; and
  $R_3$ represents methyloxy, formyloxy, acetoxy, acyloxy, S-alkoxy, acetylthio, glycinate, vinyl ether, acetoxymethyl, methyl carbonate, halogens, methyl, hydroxy, or ethyloxy.

5. The method of claim 4, wherein said compound is CDB-4124.

6. The method of claim 4, wherein said compound is administered at a dosage of 12.5 mg per day.

7. The method of claim 4, wherein said compound is administered at a dosage of 25 mg per day.

8. The method of claim 5, wherein said compound is administered at a dosage of 12.5 mg per day.

9. The method of claim 5, wherein said compound is administered at a dosage of 25 mg per day.

10. The method of claim 1, wherein said compound is administered for a period of at least six months.

11. The method of claim 1, wherein the SPRM is 17α-acetoxy-11β-(4-N,N-dimethylaminophenyl)-19-norpregna-4,9-dien-3,20-dione.

12. The method of claim 1, wherein said intermittent administration comprises administering said composition daily or every other day for a period of four months beginning during the luteal phase of said female's menstrual cycle, then discontinuing said administration by means of a continual lack of treatment for a period of days sufficient to allow the female to menstruate then administering the composition daily or every other day for a period of four months, then discontinuing said administration by means of a continual lack of treatment for a period of days sufficient to allow the female to menstruate, and repeating this pattern of administration and discontinuance of administration for as long as necessary to achieve treatment of said conditions.

* * * * *